United States Patent
Wenzel et al.

(10) Patent No.: US 8,478,403 B2
(45) Date of Patent: Jul. 2, 2013

(54) IMPLANTABLE SYSTEMS AND METHODS FOR USE THEREWITH FOR MONITORING AND MODIFYING ARTERIAL BLOOD PRESSURE WITHOUT REQUIRING AN INTRAVASCULAR PRESSURE TRANSDUCER

(75) Inventors: Brian Jeffrey Wenzel, San Jose, CA (US); Michael E. Benser, Valencia, CA (US); Taraneh Ghaffari Farazi, Santa Clara, CA (US); Timothy A. Fayram, Gilroy, CA (US); Edward Karst, South Pasadena, CA (US); Allen Keel, San Francisco, CA (US); Wenbo Hou, Lancaster, CA (US); Jong Gill, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 263 days.

(21) Appl. No.: 13/033,484

(22) Filed: Feb. 23, 2011

(65) Prior Publication Data
US 2012/0215275 A1 Aug. 23, 2012

(51) Int. Cl.
*A61N 1/00* (2006.01)

(52) U.S. Cl.
USPC .......................................................... 607/9

(58) Field of Classification Search
USPC ............... 607/9, 18; 600/301, 485, 486, 561
See application file for complete search history.

(56) References Cited

U.S. PATENT DOCUMENTS

| | | | |
|---|---|---|---|
| 4,406,289 A | 9/1983 | Wesseling et al. |
| 4,425,920 A | 1/1984 | Bourland et al. |
| 4,475,554 A | 10/1984 | Hyndman |
| 4,674,518 A | 6/1987 | Salo |
| 4,686,987 A | 8/1987 | Salo et al. |
| 4,686,988 A | 8/1987 | Sholder |
| 4,708,142 A | 11/1987 | DeCote, Jr. |
| 4,712,555 A | 12/1987 | Thornander et al. |
| 4,729,376 A | 3/1988 | DeCote, Jr. |
| 4,731,051 A | 3/1988 | Fischell |
| 4,788,980 A | 12/1988 | Mann et al. |
| 4,791,931 A | 12/1988 | Slate |
| 4,809,697 A | 3/1989 | Causey, III et al. |
| 4,940,052 A | 7/1990 | Mann et al. |
| 4,944,298 A | 7/1990 | Sholder |
| 4,944,299 A | 7/1990 | Silvian |
| 4,947,845 A | 8/1990 | Davis |
| 4,969,467 A | 11/1990 | Callaghan et al. |
| 5,334,222 A | 8/1994 | Salo et al. |
| 5,350,410 A | 9/1994 | Kleks et al. |
| 5,674,256 A | 10/1997 | Carlson |
| 5,865,755 A | 2/1999 | Golub |
| 6,120,459 A | 9/2000 | Nitzan et al. |

(Continued)

*Primary Examiner* — George Manuel
*Assistant Examiner* — Robert N Wieland

(57) ABSTRACT

Embodiments of the present invention are directed to implantable systems, and methods for use therewith, that monitor and modify a patient's arterial blood pressure without requiring an intravascular pressure transducer. In accordance with an embodiment, for each of a plurality of periods of time, there is a determination one or more metrics indicative of pulse arrival time (PAT), each of which are indicative of how long it takes for the left ventricle to generate a pressure pulsation that travels from the patient's aorta to a location remote from the patient's aorta. Based on the one or more metrics indicative of PAT, the patient's arterial blood pressure is estimated. Changes in the arterial blood pressure are monitored over time. Additionally, the patient's arterial blood pressure can be modified by initiating and/or adjusting pacing and/or other therapy based on the estimates of the patient's arterial blood pressure and/or monitored changes therein.

18 Claims, 9 Drawing Sheets

U.S. PATENT DOCUMENTS

| | | | |
|---|---|---|---|
| 6,122,536 | A | 9/2000 | Sun et al. |
| 6,275,734 | B1 | 8/2001 | McClure et al. |
| 6,409,675 | B1 | 6/2002 | Turcott |
| 6,466,821 | B1 | 10/2002 | Pianca et al. |
| 6,491,639 | B1 | 12/2002 | Turcott |
| 6,575,912 | B1 | 6/2003 | Turcott |
| 6,616,613 | B1 | 9/2003 | Goodman |
| 6,648,828 | B2 | 11/2003 | Friedman et al. |
| 6,658,292 | B2 | 12/2003 | Kroll et al. |
| 6,731,967 | B1 | 5/2004 | Turcott |
| 6,942,622 | B1 | 9/2005 | Turcott |
| 6,997,879 | B1 | 2/2006 | Turcott |
| 7,029,447 | B2 | 4/2006 | Rantala |
| 7,174,203 | B2 | 2/2007 | Arand et al. |
| 7,194,306 | B1 | 3/2007 | Turcott |
| 7,212,861 | B1 | 5/2007 | Park et al |
| 7,286,875 | B1 | 10/2007 | Park et al. |
| 7,403,813 | B1 | 7/2008 | Farazi et al. |
| 7,544,168 | B2 | 6/2009 | Nitzan |
| 7,653,434 | B1 | 1/2010 | Turcott et al. |
| 7,660,616 | B1 | 2/2010 | Poore |
| 7,840,246 | B1 | 11/2010 | Poore |
| 2002/0001390 | A1 | 1/2002 | Kawaguchi |
| 2002/0151938 | A1 | 10/2002 | Corbucci |
| 2003/0187341 | A1 | 10/2003 | Sackner et al. |
| 2004/0030261 | A1 | 2/2004 | Rantala |
| 2005/0027323 | A1* | 2/2005 | Mulligan et al. ............... 607/18 |
| 2005/0131306 | A9 | 6/2005 | Mills |
| 2005/0251059 | A1 | 11/2005 | Kim |
| 2005/0261593 | A1 | 11/2005 | Zhang et al. |
| 2006/0074322 | A1 | 4/2006 | Nitzan |
| 2007/0179541 | A1 | 8/2007 | Prakash et al. |
| 2007/0255327 | A1 | 11/2007 | Cho et al. |
| 2008/0114219 | A1 | 5/2008 | Zhang et al. |
| 2008/0262365 | A1 | 10/2008 | Bjorling |
| 2010/0016735 | A1 | 1/2010 | Harpas et al. |
| 2010/0228311 | A1* | 9/2010 | Naqvi et al. ............... 607/18 |

* cited by examiner

IMPLANTABLE SYSTEMS AND METHODS FOR USE THEREWITH FOR MONITORING AND MODIFYING ARTERIAL BLOOD PRESSURE WITHOUT REQUIRING AN INTRAVASCULAR PRESSURE TRANSDUCER

FIELD OF THE INVENTION

Embodiments of the present invention relate to implantable systems for monitoring and modifying arterial blood pressure, and methods for use therewith.

BACKGROUND OF THE INVENTION

A person's circulatory system includes both systemic and pulmonary circulation systems. Pulmonary circulation supplies the lungs with blood flow, while the systemic circulation takes care of all the other parts of the body. The heart serves as a pump that keeps up the circulation of the blood. Both the pulmonary and systemic circulatory systems are made up of arteries, arterioles, capillaries, venules and veins. The arteries take the blood from the heart, while the veins return the blood to the heart Blood pressure is defined as the force exerted by the blood against any unit area of the vessel wall. The measurement unit of blood pressure is millimeters of mercury (mmHg). Pulmonary and systemic arterial pressures are pulsatile, having systolic and diastolic pressure values. The highest recorded pressure reading is called systolic pressure (SP), which results from the active contraction of the ventricle. Although the arterial pressure and indeed flow in the arteries is pulsatile, the total volume of blood in the circulation remains constant. The lowest pressure reading is called diastolic pressure (DP) which is maintained by the resistance created by the smaller blood vessels still on the arterial side of the circulatory system (arterioles). Stated another way, the systolic pressure is defined as the peak pressure in the arteries, which occurs as a result of the ventricular contraction phase of a cardiac cycle. In contrast, the diastolic pressure is the lowest pressure, which occurs at the resting phase of the cardiac cycle. The pulse pressure (PP) reflects the difference between the maximum and minimum pressures measured (i.e., the difference between the systolic pressure and diastolic pressure). The mean arterial pressure (MAP) is the average pressure throughout the cardiac cycle.

Arterial blood pressure, such as mean arterial pressure (MAP), is a fundamental clinical parameter used in the assessment of hemodynamic status of a patient. Mean arterial pressure can be estimated from real pressure data in a variety of ways. Among the techniques that are used, two are presented below. In these formulas, SP is the systolic blood pressure, and DP is diastolic pressure.

$$MAP_2 = \frac{(SP + 2DP)}{3} = \frac{1}{3}(SP) + \frac{2}{3}(DP) \qquad \text{a.}$$

$$MAP_1 = \frac{(SP + DP)}{2}. \qquad \text{b.}$$

Systolic pressure and diastolic pressure can be obtained in a number of ways. A common approach is to use a stethoscope, an occlusive cuff, and a pressure manometer. However, such an approach is slow, requires the intervention of a skilled clinician and does not provide continuous readings as it is a measurement of systolic pressure at a single point in time and a measurement of diastolic pressure at another point in time. While systolic pressure and diastolic pressure can also be obtained in more automated fashions, it is not always practical to obtain measures of pressure using a cuff and pressure transducer combination, especially if the intention or desire is to implant a sensor that can monitor arterial pressure on a chronic basis.

Another approach for obtaining measures of arterial blood pressure is to use an intravascular pressure transducer. However, an intravascular device may cause problems such as embolization, nerve damage, infection, bleeding and/or vessel wall damage. Additionally, the implantation of an indwelling intravascular pressure transducer would require a highly skilled clinician such as a surgeon, electrophysiologist, or interventional cardiologist. Further, the cost of an intravascular pressure transducer and its implantation may not be covered by insurance, even though the cost of an ICD and/or pacemaker is covered for a patient.

Plethysmography, the measurement of volume of an organ or body part, has a history that extends over 100 years. Photoplethysmography (PPG) uses optical techniques to perform volume measurements, and was first described in the 1930s. While best known for their role in pulse oximetry, PPG sensors have also been used to indirectly measure blood pressure. For example, non-invasive PPG sensors have been used in combination with an inflatable cuff in a device known as Finapres. U.S. Pat. No. 4,406,289 (Wesseling et al.) and U.S. Pat. No. 4,475,554 (Hyndman) are exemplary patents that relate to the Finapres technique. The cuff is applied to a patient's finger, and the PPG sensor measures the absorption at a wavelength specific for hemoglobin. After the cuff is used to measure the individual's mean arterial pressure, the cuff pressure around the finger is then varied to maintain the transmural pressure at zero as determined by the PPG sensor. The Finapres device tracks the intra-arterial pressure wave by adjusting the cuff pressure to maintain the optical absorption constant at all times.

There are a number of disadvantages to the Finapres technique. For example, when there exists peripheral vasoconstriction, poor vascular circulation, or other factors, the blood pressure measured in a finger is not necessarily representative of central blood pressure. Further, maintaining continuous cuff pressure causes restriction of the circulation in the finger being used, which is uncomfortable when maintained for extended periods of time. Accordingly, the Finapres technique is not practical for chronic use. Additionally, because of the need for a pneumatic cuff, a Finapres device can not be used as an implanted sensor.

Simple external blood pressure monitors also exist, but they do not offer continuous measurement and data logging capability. These devices can be purchased at a drug store, but patient compliance is required to make regular measurements and accurately record the data. Additionally, portable external miniature monitors that automatically log blood pressure data exist, but these devices can only store a day or so of data and require clinician interaction to download and process the measured data.

As is evident from the above description, there is the need for improved systems and methods for monitoring arterial blood pressure, including systolic pressure, diastolic pressure and/or mean arterial pressure.

SUMMARY

Embodiments of the present invention are directed to implantable systems, and methods for use therewith, that monitor and modify a patient's arterial blood pressure without requiring an intravascular pressure transducer. In accordance with an embodiment, for each of a plurality of periods of time, there is a determination one or more metrics indicative of pulse arrival time (PAT), each of which is indicative of how long it takes a pulse wave to travel from the patient's aorta to a location remote from the patient's aorta. Based on the one or more metrics indicative of PAT, the patient's arterial blood pressure is estimated. Based on the estimates of the patient's arterial blood pressure, changes in the patient's arterial blood pressure are to be monitored. Additionally, the patient's arterial blood pressure is modified by initiating and/or adjusting pacing and/or other therapy based on the estimates of the patient's arterial blood pressure and/or changes therein.

In accordance with specific embodiments, for each of a plurality of periods of time per day during which the patient's heart is being paced, a signal indicative of electrical activity of the patient's heart (e.g., an IEGM signal), and a signal indicative of changes in arterial blood volume remote from the patient's heart (e.g., a PPG signal) are obtained. One or more predetermined features of the signal indicative of electrical activity of the patient's heart is/are detected, and one or more predetermined features of the signal indicative of changes in arterial blood volume remote from the patient's heart is/are detected. One or more metrics indicative of PAT are determined by determining a time from one of the detected features of the signal indicative of electrical activity of the patient's heart to one of the detected features of the signal indicative of changes in arterial blood volume remote from the patient's heart. The patient's arterial blood pressure is estimated based on at least one of the metric(s) indicative of PAT. Changes in the patient's arterial blood pressure are monitored based on the estimates of the patient's arterial blood pressure. In a specific embodiment, the patient's arterial blood pressure is modified by adjusting at least one pacing parameter and/or pacing configuration based on the monitored changes in the patient's arterial blood pressure. To increase arterial blood pressure, a pacing rate can be increased, an atrio-ventricular (AV) interval can be reduced and/or pacing at an additional pacing site within the left ventricular chamber can be initiated. To reduce arterial blood pressure, the pacing rate can be reduced, the AV interval can be increased and/or pacing at one of multiple pacing sites within the left ventricular chamber can be stopped.

In accordance with an embodiment, monitoring changes in the patient's arterial pressure includes monitoring a circadian variability of the patient's arterial blood pressure. If the circadian variability is below a first threshold (indicating that the circadian variability is too low), one or more adjustments to pacing parameter(s) and/or pacing configuration can be made to increase the circadian variability. If the circadian variability is above a second threshold (indicating that the circadian variability is too high), one or more adjustments to pacing parameter(s) and/or pacing configuration can be made to decrease the circadian variability. In a specific embodiment, one or more adjustments to pacing parameter(s) and/or pacing configuration are made to cause the circadian variability pattern of the patient's arterial blood pressure to track a predetermined circadian variability pattern.

In accordance with an embodiment, changes in the patient's activity level are also monitored. This enables one or more adjustments to pacing parameter(s) and/or pacing configuration to be made based on the monitored changes in the patient's arterial blood pressure and based on the monitored changes in the patient's activity level. For example, pacing parameter(s) and/or pacing configuration can be adjusted to increase the patient's arterial blood pressure if an increase in the patient's arterial blood pressure is too low for the detected change in the patient's activity level. Conversely, pacing parameter(s) and/or pacing configuration can be adjusted to decrease the patient's arterial blood pressure if the patient's arterial blood pressure is too high for the detected change in the patient's activity level.

In accordance with an embodiment, changes in the patient's body position are also monitored. This enables one or more adjustments to pacing parameter(s) and/or pacing configuration to be made based on the monitored changes in the patient's arterial blood pressure and based on the monitored changes in the patient's body position. For example, pacing parameter(s) and/or pacing configuration can be adjusted to increase the patient's arterial blood pressure when a change from a supine body position to a vertical body position is detected. More generally, pacing parameter(s) and/or pacing configuration can be adjusted to increase the patient's arterial blood pressure if the change in the patient's arterial blood pressure is too low for the detected change in the patient's body position. Conversely, pacing parameter(s) and/or pacing configuration can be adjusted to decrease the patient's arterial blood pressure if the change in the patient's arterial blood pressure is too high for the detected change in the patient's body position.

Alternative therapy for increasing and decreasing (and more generally, modifying) the patient's arterial blood pressure are also possible. For example, to reduce arterial blood pressure, neurostimulation configured to cause vasodilation can be delivered, and to increase arterial blood pressure neurostimulation configured to restrict blood vessels can be delivered. For another example, a drug pump can be used to deliver medication to modify arterial blood pressure. Such alternative types of therapy can supplement or supplant the pacing therapy adjustments.

Embodiments of the present invention can also be used to track cardiovascular risk and/or disease progression based on the monitored changes in the patient's arterial blood pressure.

Additional and alternative embodiments, features and advantages of the invention will appear from the following description in which the preferred embodiments have been set forth in detail, in conjunction with the accompanying drawings and claims.

DETAILED DESCRIPTION OF THE PREFERRED EMBODIMENTS

Figure 1A:
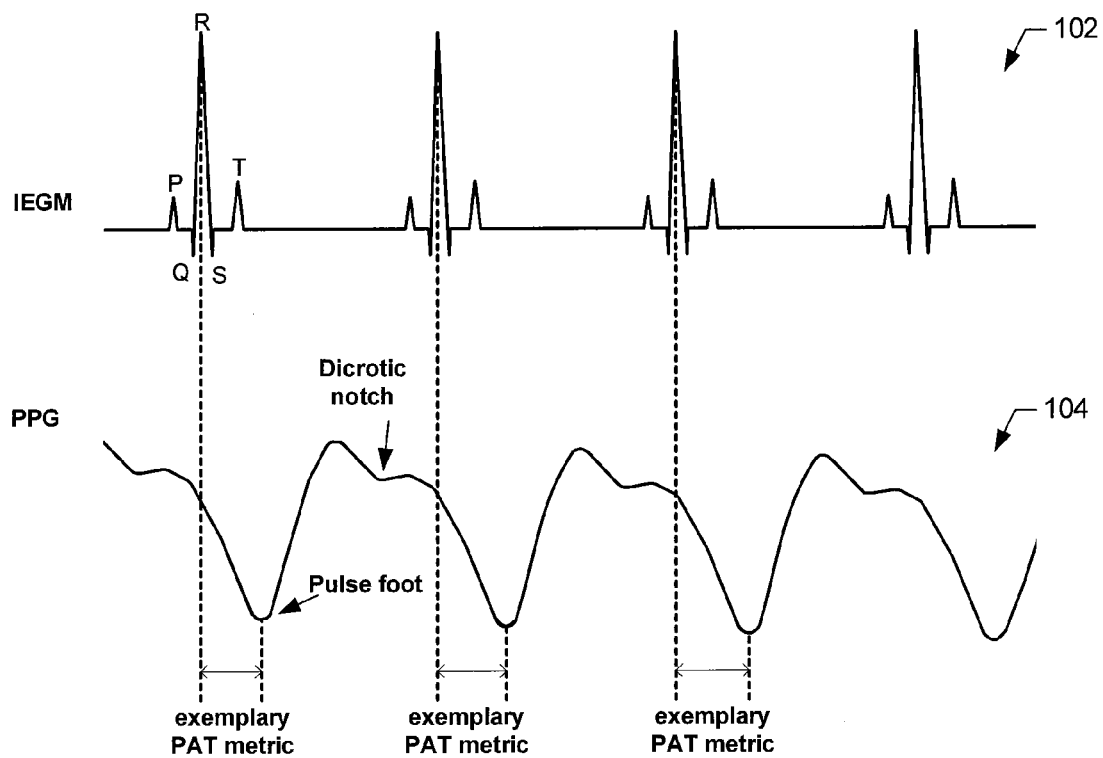
FIG. 1A includes exemplary signal waveforms that are used to show the relative timing of various signals, and how an exemplary metric indicative of pulse arrival time (PAT) can be determined in accordance with an embodiment of the present invention.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

It would be apparent to one of skill in the art that the present invention, as described below, may be implemented in many different embodiments of hardware, software, firmware, and/or the entities illustrated in the figures. Any actual software, firmware and/or hardware described herein is not limiting of the present invention. Thus, the operation and behavior of the present invention will be described with the understanding that modifications and variations of the embodiments are possible, given the level of detail presented herein.

Figure 1B:
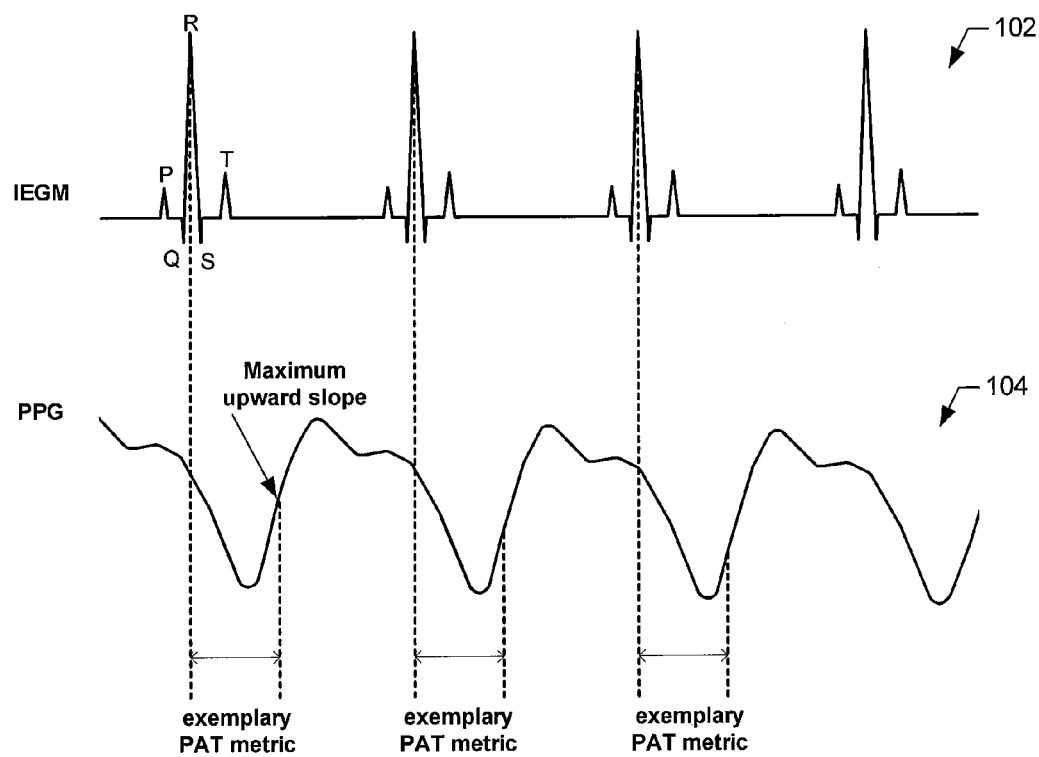
FIG. 1B includes the same exemplary signal waveforms shown in FIG. 1A, but shows how another metric indicative of PAT can be determined in accordance with an embodiment of the present invention.
Figure 1C:
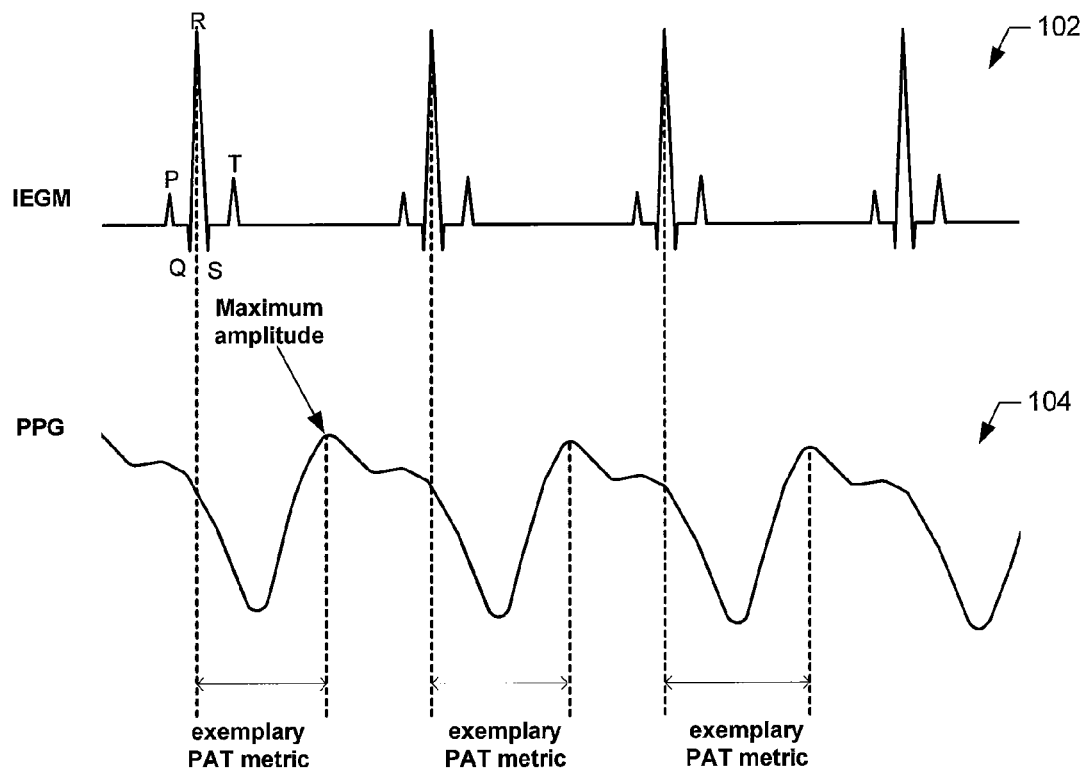
FIG. 1C includes the same exemplary signal waveforms shown in FIG. 1A, but shows how still another exemplary metric indicative of PAT can be determined in accordance with an embodiment of the present invention.

In accordance with specific embodiments of the present invention, an intracardiac electrogram (IEGM), e.g., like 102 in FIGS. 1A-1C, is obtained using implanted electrodes. Additionally, a plethysmography signal, e.g., a photoplethysmography (PPG) signal like 104 in FIGS. 1A-1C, is obtained from an implanted sensor. In accordance with specific embodiments of the present invention, by detecting the relative timing and optionally amplitude of certain features of such signals, various estimates of arterial blood pressure can be obtained, including systolic pressure (SP), diastolic pressure (DP), pulse pressure (PP) and/or mean arterial pressure (MAP).

The SP is the peak pressure in the arteries, which occurs as a result of the ventricular contraction phase of a cardiac cycle. The DP is the lowest pressure in the arteries, which occurs at the end of the resting phase of the arterial circulation. This corresponds to the end of the filling phase of the cardiac cycle with respect to ventricular function. The PP is the difference between the systolic and diastolic pressures. The MAP is a weighted average of pressure throughout the cardiac cycle.

Because implanted electrodes and an implanted sensor are used to estimate arterial blood pressure, a patient's arterial blood pressure can be monitored on a chronic basis. Thus, arterial blood pressure can be estimated multiple times a day to identify blood pressure fluctuations, such as circadian variability. Additionally, arterial blood pressure changes associated with a change in pacing parameters can be monitored.

Additionally, embodiments of the present invention can be used to track a patient's arterial blood pressure to monitor a patient's worsening (or improving) cardiac disease state, and to trigger alerts (e.g., in response to which a patient may take blood pressure medications). Additionally, arterial blood pressure estimates can be used as a measure of hemodynamic function.

A plethysmography signal is an example of a signal that is indicative of change in arterial blood volume, and is typically inverted in post-processing. Thus the peak in a plethysmography signal occurs corresponding to the peak in local arterial blood pressure, when blood vessels are distended with larger blood volume. This is because the peak in the plethysmography signal is indicative of the peak wave in arterial blood pressure generated by the patient's heart, as detected by a sensor (e.g., an extravascular PPG sensor) located a distance from the patient's heart. Presuming, e.g., that an extravascular PPG sensor is implanted in the pectoral region of the patient (which is an option, but not necessary), the time it takes from ventricular electrical activation detected by implanted electrodes to develop a pressure wave that travels from the patient's heart to the PPG sensor can be, e.g., on the order of ~100-300 msec, depending on the location of the electrodes (used to obtain the IEGM) and the location of the PPG sensor. The peak pressure wave is initially detectable from an IEGM obtained using implanted electrodes. The time at which the peak wave reaches the implanted PPG sensor is detectable from a PPG signal produced by the implanted PPG sensor. Accordingly, the amount of time it takes a peak pulse wave to travel from the patient's heart to the PPG sensor can be determined. Such information has been shown to correlate to arterial blood pressure. It is also possible, and within the scope of the present invention, that the time it takes a peak pulse to travel from the patient's heart to the PPG sensor can be outside the 100-300 msec range mentioned above.

The amount of time it takes for a pulse wave to travel from a patient's heart (and more specifically, their aorta) to a location remote from the patient's heart is often referred to as pulse arrival time (PAT). Embodiments of the present invention use the concept of PAT (also known as pulse transmit time, or pulse wave velocity) to monitor arterial blood pressure. However, embodiments of the present invention differ from prior art non-implanted systems that rely on PAT, e.g., because such prior are systems are not practical for chronic use.

The inventors of the present invention are aware of one prior art reference, i.e., U.S. Pat. No. 4,425,920 (Bourland et al.), that does suggest an implantable system for monitoring arterial blood pressure using the concept of PAT. However, the system of the '920 patent requires that two sets of electrodes be positioned adjacent a same artery at two sites, and thus, requires very precise and potentially difficult implantation of its system. In contrast, the implantable systems of many of the embodiments of the present invention can be implanted in the same manner as a conventional pacemaker, ICD or implantable hemodynamic monitor, for which there are many physicians trained to perform such implants.

Referring to FIG. 1A, the representative signal waveforms therein are used to show the relative timing of a signal indicative of electrical activity of the patient's heart and a signal indicative of changes in arterial blood volume remote from the patient's heart. The upper most waveform is representative of an intracardiac electrogram (IEGM) signal 102, which is indicative of electrical activity of the patient's heart. The lower waveform is representative of a photoplethysmography (PPG) signal 104, which is indicative of changes in arterial blood volume.

Referring to the IEGM signal 102, each cycle of the signal 102 is shown as including a P wave, a QRS complex (including Q, R and S waves) and a T wave. The P wave is caused by depolarization of the atria. This is followed by atrial contraction, during which expulsion of blood from the atrium results in further filling of the ventricle. Ventricular depolarization, indicated by the QRS complex, initiates contraction of the ventricles resulting in a rise in ventricular pressure until it exceeds the pulmonary and aortic diastolic blood pressures to result in forward flow as the blood is ejected from the ventricles. Ventricular repolarization occurs thereafter, as indicated by the T wave and this is associated with the onset of ventricular relaxation in which forward flow stops from the ventricles into the aorta and pulmonary arteries. Thereafter, the pressure in the ventricles falls below that in the atria at which time the mitral and tricuspid valves open to begin to passively fill the ventricles during diastole. Depending on the sensing vector(s) used to obtain the IEGM signal, some of the above mentioned waves may not be detectable. For example, it may be that only an R-wave is reliably detectable from the IEGM signal.

An exemplary metric indicative of pulse arrival time (PAT) is also shown in FIG. 1A. In general, an metric indicative of PAT can be determined, in accordance with embodiments of the present invention, by determining a time from a detected predetermined feature of an IEGM signal (e.g., 102) to a detected predetermined feature of the signal indicative of changes in arterial volume, which can be a PPG signal (e.g., 104), but is not limited thereto. The predetermined feature of the signal indicative of cardiac electrical activity is preferably indicative of ventricular depolarization. The predetermined feature of the signal indicative of arterial blood volume is preferably indicative of the systolic portion of the signal. In FIG. 1A, the predetermined feature of the IEGM signal 102 is the R-wave, and the predetermined feature of the PPG signal 104 is the pulse foot that occurs just prior to the start of local blood volume increase. In other words, the metric indicative of PAT can be determined by determining a time from the R-wave of the IEGM signal 102 to the pulse foot of the PPG signal 104, as illustrated in FIG. 1A. Alternatively, as illustrated in FIG. 1B, the metric indicative of PAT can be determined by determining a time from the R-wave of the IEGM signal 102 to the maximum upward slope of the PPG signal 104. As illustrated in FIG. 1C the metric indicative of PAT can be determined by determining a time from the R-wave to the maximum amplitude of the PPG signal 104. A metric indicative of PAT can also be referred to as a PAT metric. Additional or alternative PAT metrics, besides those described with reference to FIGS. 1A-1C, may be determined.

As described above in FIGS. 1A-1C, the metric indicative of PAT can be determined by determining a time from a detected predetermined feature of an IEGM signal to a detected predetermined feature of the PPG signal. In accordance with an embodiment, a predetermined feature of the IEGM signal and/or a predetermine feature of the PPG signal can be determined using a wavelet transformation, which can provide a consistent and robust technique to detect the predetermined feature(s) of the IEGM and/or PPG signal used in determining estimates of arterial blood pressure. Wavelet transformation techniques are well known, and thus need not be described herein.

Figure 2:
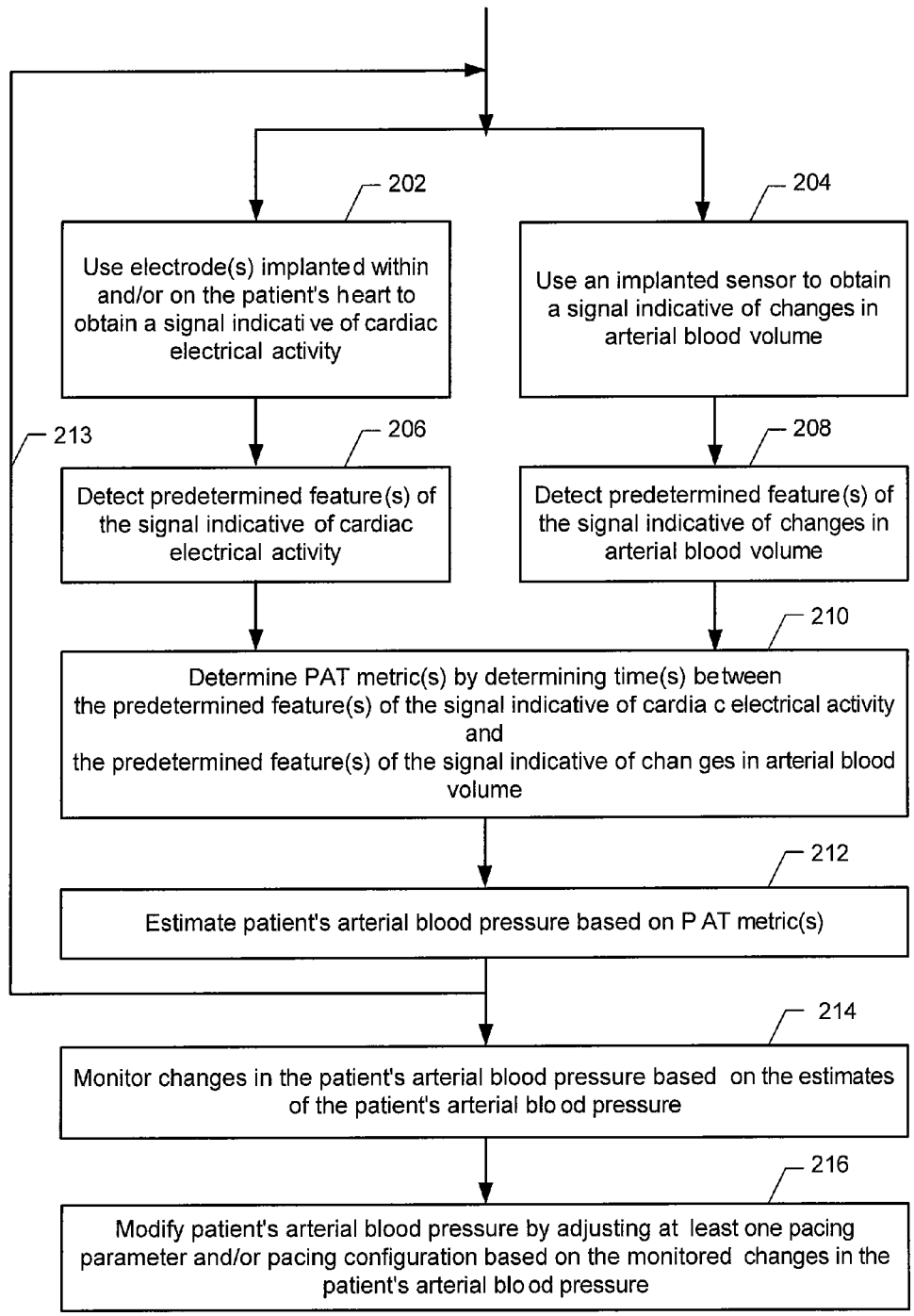
FIG. 2 is a high level flow diagram that is used to explain various embodiments of the present invention that can be used to monitor and modify a patient's arterial blood pressure without requiring an intravascular pressure transducer.

The high level flow diagram of FIG. 2 will now be used to explain various embodiments of the present invention that can be used to monitor and modify a patient's arterial blood pressure without requiring an intravascular pressure transducer. Such embodiments can be implemented by an implantable system, examples of which are discussed below with reference to FIGS. 3 and 4. In FIG. 2 and the other flow diagrams described herein, the various algorithmic steps are summarized in individual 'blocks'. Such blocks describe specific actions or decisions that are made or carried out as the algorithm proceeds. Where a microcontroller (or equivalent) is employed, the flow diagram presented herein provides the basis for a 'control program' that may be used by such a microcontroller (or equivalent) to effectuate the desired control of the implantable system. Those skilled in the art may readily write such a control program based on the flow diagram and other descriptions presented herein.

Referring to FIG. 2, at steps 202 and 204, one or more electrodes implanted within and/or on the patient's heart is/are used to obtain a IEGM signal indicative of cardiac activity, and an implanted extravascular sensor (e.g., optical sensor, which can also be referred to as a PPG sensor) is used to obtain a signal indicative of changes in arterial blood volume. The signal indicative of changes in arterial blood volume obtained at step 204 can be a PPG signal or some other plethysmography signal. An optical sensor can be used to obtain a PPG signal. Examples of electrodes and circuitry that can be used to obtain an IEGM signal are discussed below with reference to FIGS. 3 and 4. Exemplary sensors that can be used to obtain a PPG signal are discussed below with reference to FIGS. 3 and 4.

In still other embodiments, the plethysmography signal indicative of changes in arterial blood volume can be a signal output by a sensor including a piezo-electric diaphragm. Alternative sensors that can be used to produce the plethysmography signal indicative of changes in arterial blood volume, include, but are not limited to, a close range microphone, a sensor including a small mass on the end of a piezo bending beam with the mass located on the surface of a small artery, a transmission mode infrared motion sensor sensing across the surface of a small artery, or a MEMS accelerometer located on the surface of a small artery. Such alternative sensors can be located, e.g., on the tip of a short lead connected to a device that is subcutaneously implanted. The implanted sensor is preferably close to the patient's aorta. For example, it is preferred that the implanted sensor (used to obtain the signal indicative of changes in arterial blood volume) is 10 mm from the patient's aortic root. Such a sensor can be implanted, e.g., in the pectoral region of a patient. An alternative location for implantation of the sensor includes, but is not limited to, the patient's abdominal region. It is also possible that the signal indicative of changes in arterial blood volume is an impedance plethysmography signals (IPG) obtained using implanted electrodes (in which case such electrodes can be considered part of a plethysmography sensor). For the remainder of this discussion, it will be assumed that the signal obtained at step 204 is a PPG signal. However, as just explained above, alternative plethysmography signals can be used.

Still referring to FIG. 2, at steps 206 and 208, one or more predetermined features of the signal indicative of cardiac electrical activity is/are detected, and one or more predetermined features of the signal indicative of changes in arterial blood volume (e.g., the PPG signal) is/are detected. The one or more predetermined features of the EGM signal, detected at step 206, can include features indicative of ventricular depolarization, such as a Q-wave, an R-wave and/or an S-wave of the IEGM signal, and/or a QRS complex of the IEGM signal, but is not limited thereto. However, since the R wave is the easiest to detect, due to its relatively large magnitude, it is often most practical for ventricular depolarization to be detected by detecting the R wave. Accordingly, any known or future developed technique for detecting an R wave (e.g., by peak detection or threshold crossing) can be used to detect ventricular depolarization. Exemplary techniques for detecting R waves are discussed with reference to FIGS. 4-8 of U.S. Pat. No. 7,403,813, entitled "Systems and Methods for Detection of VT and VF from Remote Sensing Electrodes" (Farazi et al.), which is incorporated herein by reference. Alternatively, known or future developed techniques for detecting the Q, R and/or S waves can be used to detect ventricular depolarization.

At step 208, the one or more predetermined features of the PPG signal can correspond to a systolic portion of the signal. The morphology of the PPG signal is relatively consistent beat to beat, especially around the systolic portion of the signal. This consistency of the morphology around the systolic portion of the signal can allow for robust and reliable selection of a predetermined feature that can serve as a basis for determining a metric indicative of PAT. In accordance with an embodiment, the one or more predetermined features of the PPG signal can include the pulse foot of the PPG signal, the pulse peak of the PPG signal, and/or the maximum positive slope of the PPG signal, but is not limited thereto.

As will be discussed below, in certain embodiments it is also useful to determine the peak-to-peak amplitude a1 (shown in FIG. 1C) of the plethysmography signal. One or more peak detection circuit can be used to detect the peak-to-peak amplitude a1. Alternatively, software, hardware and/or firmware can be used to detect the peak-to-peak amplitude a1 based on sample data points of the plethysmography signal, e.g., by determining a difference between maximum and minimum sample values of a plethysmography signal for each cardiac cycle, or a similar algorithm. An exemplary peak-to-peak amplitude a1 is shown in FIG. 1C.

As was discussed above, in accordance with certain embodiments, wavelet transformations can be used to detect a predetermined feature(s) of the IEGM signal and/or PPG signal used in determining the metric indicative of PAT.

With reference back to FIG. 1C, at step 208, the metric indicative of PAT can be determined by determining a time from detection of the ventricular depolarization (detected by detecting an R-wave) to the detection of the maximum peak amplitude in a plethysmography signal. Ventricular depolarization occurs at the beginning of systole, which substantially coincides with the end of diastole. The maximum peak amplitude of the plethysmography signal occurs when a mechanical pulse resulting from the ventricular depolarization is detected by the plethysmography sensor, which is a distance from a location in the patient's heart where the pulse originated. For example, the plethysmography sensor (e.g., a PPG sensor) can be implanted in the pectoral region, e.g., attached directly to (or by a lead to) a housing of an implanted device, as described below with reference to FIG. 3.

At step 210, one or more metric indicative of PAT is/are determined, where each metric indicative of PAT is determined by determining a time from one of the predetermined features of the signal indicative of cardiac electrical activity (e.g., an IEGM signal) to one of the predetermined features of the signal indicative of changes in arterial blood volume (e.g., a PPG signal) As mentioned above, a metric indicative of PAT can also be referred to as the PAT metric. In accordance with specific embodiments of the present invention, the PAT metric can be determined by determining a time from a predetermined feature indicative of ventricular depolarization of the signal indicative of cardiac electrical activity to a predetermined feature corresponding to a systolic portion of the signal indicative of changes in arterial blood volume. For example, where the metric indicative of PAT is the time from an R-wave to the peak of the PPG signal (as in FIG. 1C), the metric indicative of PAT is indicative of the time from the beginning of systole (or end of diastole) to the peak in the mechanical pulse detected by an implanted sensor.

At step 212, the patient's arterial blood pressure is estimated based on at least one of the one or more metrics indicative of PAT.

In the certain embodiments, at step 210 one metric indicative of PAT is determined (e.g., the time from an R-wave to a peak of a PPG signal) and used to estimate arterial blood pressure at step 212. A scaling factor or simple equation can be used to estimate the patient's arterial blood pressure based on the PAT metric. In such embodiments, the PAT metric can be determined using an IEGM signal and a plethysmography signal that are each averaged over multiple cycles, or the PAT metric can be determined for each of multiple cycles and then averaged.

In other embodiments, more than one PAT metric is determined, e.g., the time from an R-wave to a foot of a PPG signal, and the time from an R-wave to a peak of a PPG signal. In such embodiments, the multiple PAT metrics can be averaged (equally, or using a weighted average), and a scaling factor or simple equation can be used to determine the estimate of the patient's arterial blood pressure based on the averaged PAT metric. Alternatively, an equation that uses multiple PAT metrics can be used to estimate the patient's arterial blood pressure. In such embodiments, the multiple PAT metrics can be determined using an IEGM signal and a plethysmography signal that are each averaged over multiple cycles, or the PAT metrics are determined for each of multiple cycles and then averaged.

At step 212 general estimates of arterial blood volume can be determined, so that changes in such general estimates can be detected. It is also within the scope of the present invention that estimates of SP, DP, PP and/or MAP be determined, as will now be explained. PAT is inversely related to SP, in that the greater the PAT the lower the SP, and the lower the PAT the greater the SP. In a simplest embodiment, SP≈1/(PAT metric). However, it would be preferred to use a patient specific correlation factor (e.g., a constant K) when determining SP. In other words, in specific embodiments, SP=K/(PAT metric), where K is determined during a calibration procedure. During such a calibration procedure, an actual value of SP can be determined using any known accurate acute technique, and a PAT metric is measured in the manner described above using an implanted system. This will result in K being the only unknown factor in the equation, and thus, K would be easily calculable (e.g., by an external programmer, or the like). The patient could also be asked to exercise, or could be appropriately paced, to change the patient's SP, to thereby check the accuracy of K over a range of SPs and PAT metrics. If appropriate, K can be adjusted so that K is accurate over a range of systolic pressures. Presuming the PAT metric is measured in msec, the units of K can be mmHg·msec, so that when K is multiplied by 1/(PAT metric), the resulting SP has units of mmHg. Use of look up tables and interpolation are also within the scope of the present invention.

In summary, at step 212, SP can be determined based on a PAT metric using an equation (e.g., SP=K/PAT metric), or using a simple look-up table. An alternative equation could be SP=K/(PAT metric)+β. In a similar manner as just described, β can be determined during a calibration procedure. It is also possible that K and/or β can be determined for a patient population instead of for individual patients. Other formulas are also possible, and could be derived by determining actual values of the SP for various different values of the PAT metric, and are within the scope of the present invention.

An exemplary calibration procedure (performed at implant and/or thereafter) will now be explained. During the calibration procedure, actual measures of arterial blood pressure, including SP and DP, are measured along with values of PAT metrics (and optionally peak-to-peak amplitude a1, as will be discussed below). The actual measure of the patient's SP and DP can be obtained, e.g., using a non-invasive auscultatory or oscillometric techniques, or an acute invasive intravascular cannula method, or any other acute technique. For a more specific example, actual arterial pressure measurements (SP and DP) can be measured using a high fidelity micronometer-tipped pressure catheter (e.g., model 4F, SPC-120, available from Millar Instruments, Texas), which is temporarily placed in the ascending aorta via a carotid arteriotomy. Other techniques are also possible, and within the scope of the present invention.

A value indicative of pulse pressure (PP) can be determined based on the amplitude a1. A value indicative of diastolic pressure (DP) can be determined by subtracting the value indicative of PP from the value indicative of SP (i.e., DP=SP−PP). The value indicative of PP is mainly determined so that the value of DP can be determined. Accordingly, a value of DP can be determined based on the value of SP and the value of a1.

Peak-to-peak amplitude a1 is directly related to the PP, in that the greater a1 the greater the PP, and the lower the a1 the lower the PP. In a simplest embodiment, PP≈a1. However, it would be preferred to use a patient specific correlation factor (e.g., a constant M) when determining PP. In other words, in specific embodiments, PP=M·a1, or possibly PP=M·a1+σ, where M (and possibly also a) can be determined during a calibration procedure, as will be described below. During calibration, while actual values of SP are being determined for various PAT metrics, actual values of DP can also be determined for various values of a1. This will enable the patient specific correlation factor M (and possibly also σ) to be determined during the calibration procedure. For example, by combining PP=M·a1 with DP=SP−PP, a resulting equation is DP=SP−(M·a1). Since actual values of DP and SP can be obtained during calibration (at implant and/or thereafter), and values of a1 can be measured during calibration, the patient specific correlation factor M (and possibly also a) can be easily determined. It is also possible that M and/or a can be determined for a patient population instead of for individual patients. Other formulas are also possible, and could be derived by determining actual values of the DP for various different values of a1. After implant, in similar manners as were discussed above, an algorithm or look-up table can be used to calculate PP based on a1.

If both SP and DP are estimated, mean arterial pressure (MAP) can also be estimated. For example, the equation MAP=1/3SP+2/3DP can be used. Alternatively, the equation MAP=(SP+DP)/2 can be used. Use of other equations is also within the scope of the present invention.

As indicated by line 213, steps 202, 204, 206, 208, 210 and 212 can be repeated from time to time (e.g., periodically, aperiodically, in response to a triggering event, etc.), with an estimate of the patient's arterial blood pressure being determined each time. In specific embodiments these steps are performed multiple times a day, e.g., one per hour or other interval of time.

At step 214, changes in the patient's arterial blood pressure are monitored based on the estimates of the patient's arterial blood pressure. This can include, e.g., detecting increases or decreases in the patient's arterial blood pressure, or detecting that the patient's arterial blood pressure has not changed. As will be described below, step 214 can also include detecting circadian variability in arterial blood pressure and/or fluctuations over shorter or longer periods.

At step 216, the patient's arterial blood pressure is modified by adjusting at least one pacing parameter and/or pacing configuration based on the monitored changes in the patient's arterial blood pressure. Various factors that may trigger the adjusting of pacing parameter(s) and/or pacing configuration at step 216 are described below. For example, estimates of arterial blood pressure and/or changes therein can be compared to one or more thresholds to identify when it would be useful to modify the patient's arterial blood pressure to keep it more in line with a desired value or range. Various ways to modify arterial blood pressure at step 216 are also described below.

There are numerous reasons why it could be valuable to monitor changes in a patient's arterial blood pressure and to modify a patient's blood pressure. For example, patients with heart failure (HF) and compromised systolic function may supply an inadequate amount of blood to organs of the body. For such patients, it may be desirable to maintain blood pressure. Other patients may have hypertension or compromised diastolic function, and thus have elevated blood pressure. For such patients, it may be desirable to reduce blood pressure. As discussed in further detail below, there are some patients that may have orthostatic hypotension, which is a reduction in blood pressure upon changing from supine to standing position. For such patients, it may be desirable to selectively increase blood pressure in response to a change in body position. Many patients are taking medications to control blood pressure and cardiovascular properties, but may not be in compliance at all times. For such patients, it may be desirable to provide a backup way of controlling blood pressure for those times that the patient is not in compliance. Embodiments of the present invention described herein can be used to achieve these and other goals.

In accordance with an embodiment, to increase arterial blood pressure, a pacing rate can be increased and/or an atrio-ventricular (AV) interval can be reduced. Where the implantable system is capable of performing multi-site left ventricular (MSLV) pacing, it may also be possible to increase the patient's arterial blood pressure by pacing at an additional pacing site within the left ventricular chamber. To reduce arterial blood pressure, a pacing rate can be reduced and/or the AV can be increased. Where the implantable system is capable of performing MSLV pacing, it may also be possible to reduce the patient's arterial blood pressure by stopping pacing at one of multiple pacing sites within the left ventricular chamber. Other pacing intervals can be adjusted to modify the patient's blood pressure, including, but not limited to, interventricular (VV) delay, and intraventricular delay (e.g. LV1-LV2 delay where MSLV pacing is performed). In general, adjustments that increase pumping efficiency should increase arterial blood pressure, and adjustments that decrease pumping efficiency should decrease arterial blood pressure. Other techniques for adjusting pumping efficiency include, but are not limited to, adjusting pacing site locations within the left ventricular chamber.

Use of alternative therapy for increasing or decreasing (and more generally, modifying) the patient's arterial blood pressure are also within the scope of the present invention. For example, additionally, or alternatively, to reduce arterial blood pressure, neurostimulation configured to cause vasodilation can be delivered, and to increase arterial blood pressure neurostimulation configured to restrict blood vessels can be delivered. For another example, if an implantable system is equipped with a medication pump (also known as a drug pump), such a pump can be used to deliver medication to modify arterial blood pressure. Other types of therapy can also be delivered to modify (increase or decrease) arterial blood pressure as needed while still being within the scope of the present invention. Such alternative types of therapy can supplement or supplant the pacing therapy adjustments made at step 216.

The circadian variability associated with healthy individuals involves arterial blood pressure rising in the morning and falling in the evening. Abnormalities in this circadian variability have been shown to be an independent risk factor for heart disease and stroke, even in apparently healthy individuals without chronic disease. For example, excessive swings in blood pressure (e.g., beyond an acceptable range) can be indicative of a patient having a high risk for cardiovascular disease, especially where the patient is pre-diabetic. Additionally, extraordinary short term oscillations in blood pressure can be detrimental to patients.

Embodiments of the present invention can be used to monitor a circadian variability of a patient's arterial blood pressure, and to modify the circadian variability if appropriate. More specifically, in accordance with certain embodiments, step 214 includes monitoring a circadian variability of the patient's arterial blood pressure, and step 216 includes adjusting pacing parameter(s) and/or pacing configuration to increase the circadian variability if the circadian variability is below a first threshold, and/or adjusting pacing parameter(s) and/or pacing configuration to decrease the circadian variability if the circadian variability is above a second threshold. Additionally, or alternatively, step 216 can include adjusting pacing parameter(s) and/or pacing configuration to cause the circadian variability pattern of the patient's arterial blood pressure to track a predetermined circadian variability pattern. Exemplary ways to increase or reduce arterial blood pressure by adjusting pacing parameters and/or pacing configuration were discussed above, and thus need not be repeated. Alternative types of therapy (some examples of which were discussed above) can also be delivered to modify the circadian variability of a patient's arterial blood pressure, which can supplement or supplant the pacing therapy adjustments made at step 216.

If the circadian variability of the patient's arterial blood pressure is too large, this can be indicative of disease and/or disease progression. In accordance with an embodiment, metric(s) indicative of how often and/or to what extent the circadian variability of the patient's arterial blood pressure exceeds a threshold can be monitored and tracked, which can be indicative of cardiovascular risk and disease progression. Where such metric(s) exceed thresholds indicative of excessive risk or disease progression, an alarm can be triggered. In accordance with an embodiment, an alert triggering mechanism can be part of an implanted system (e.g., patient alert 419 in FIG. 4). Alternatively or additionally, an implanted system can trigger a non-implanted alarm of a non-implanted system. In still other embodiments, where arterial blood pressure information is transmitted, e.g., via telemetry to an external device, a non-implanted alert can be triggered to thereby notify the patient and/or the patient's physician of cardiovascular risk and/or disease progression.

When a patient is inactive a patient's arterial blood pressure should be relatively low, and when the patient is active their arterial blood pressure should be correspondingly higher. This is in part because a person's muscles need more blood to operate efficiently when the patient is active (e.g., exercising). The arterial blood pressure in a patient having chronotropic incompetence may not appropriately adjust to the patient's activity level, which can result in the patient easily becoming fatigued.

In accordance with certain embodiments of the present invention, the desired blood pressure for a patient can be a function (e.g., a monotonic function) of the patient's activity level as determined using an activity sensor or some other technique. Exemplary activity sensors are discussed below with reference to FIG. 4. The patient's actively level and/or changes therein can be monitored, and step 216 can include adjusting pacing parameter(s) and/or pacing configuration based on the monitored changes in the patient's arterial blood pressure (as detected at step 214) and based on the monitored changes in the patient's activity level. For example, pacing parameter(s) and/or pacing configuration can be adjusted to increase the patient's arterial blood pressure if an increase in the patient's arterial blood pressure is too low for the detected change in the patient's activity level. Conversely, pacing parameter(s) and/or pacing configuration can be adjusted to decrease the patient's arterial blood pressure if the patient's arterial blood pressure is too high for the detected change in the patient's activity level. Alternative types of therapy (some examples of which were discussed above) can be delivered to appropriately modify the patient's arterial blood pressure, which can supplement or supplant the pacing therapy adjustments made at step 216.

A patient's arterial blood pressure should increase when the patient changes from a supine position to a vertical (e.g., sitting or standing) position. If the patient's arterial blood pressure does not sufficiently increase during such a change, the patient may be unable to perfuse the head adequately and may possibly faint. Conversely, a patient's arterial blood pressure should decrease when they change from a vertical position to a supine position. Patient's whose arterial blood pressure (which is a function of cardiac output) does not appropriately change with posture may have chronotropic incompetence or depressed vasopressor response. For instance, one type of chronotropic incompetence is vasovagal syncope in which a person's blood pressure drops when they change from a supine to a vertical position, sometimes resulting in fainting.

In accordance with certain embodiments, a patient's body position and/or changes therein is monitored, and step 216 includes adjusting pacing parameter(s) and/or pacing configuration based on the monitored changes in the patient's arterial blood pressure and based on the monitored changes in the patient's body position (also referred to as posture). This can include adjusting pacing parameter(s), pacing configuration and/or other therapy to increase the patient's arterial blood pressure when a change from a supine body position to a vertical body position is detected. In accordance with an embodiment, step 216 includes adjusting pacing parameter(s), pacing configuration and/or an alternative therapy to increase the patient's arterial blood pressure if the change in the patient's arterial blood pressure is too low for the detected change in the patient's body position. Step 216 can also include adjusting pacing parameter(s) and/or pacing configuration to decrease the patient's arterial blood pressure if the change in the patient's arterial blood pressure is too high for the detected change in the patient's body position.

In certain embodiments, a patient's desired blood pressure can be a function of both the patient's activity level and posture, and pacing parameter(s), pacing configuration and/or an alternative therapy is/are adjusted to track the desired blood pressure. The patient's desired blood pressure for a specific activity level and/or posture can be defined by a single value, or preferably, a range of arterial blood pressures values. In other words, one or more thresholds can be used to define when the patient's arterial blood pressure, or changes therein, are too high or too low for a specific body position and/or activity level, and/or change(s) therein.

If the patient's arterial blood pressure does not change proportionally with the patient's activity and/or posture, this can be indicative of disease and/or disease progression. In accordance with an embodiment, metric(s) indicative of how often and/or to what extent the patient's arterial blood pressure falls below and/or above a desired range corresponding to the patient's activity and/or posture can be monitored and tracked, which can be indicative of cardiovascular risk and disease progression. Where such metric(s) exceed thresholds indicative of excessive risk or disease progression, an alarm can be triggered. Additionally, or alternatively, pacing and/or other therapy can be triggered and adjusted.

In certain embodiments, various thresholds can be used to trigger the performance of all or certain steps of FIG. 2. For example, depending on the frequency, periodic monitoring of arterial blood pressure may be costly in terms of energy, memory and/or processing resources. Accordingly, it may be more efficient to trigger the performance of certain steps upon detection of an event, such as a specific activity, or lack thereof, and/or a specific posture of the patient. For example, an activity sensor and/or posture sensor (e.g., sensor 415 in FIG. 4) can be used to trigger the performance of the steps of FIG. 2. For example, the steps of FIG. 2 can be triggered when it is detected that a patient is inactive and lying down. Additionally, or alternatively, such steps can be triggered when a patient is upright and walking. In still other embodiments, such steps can be triggered to occur, at specific intervals following a patient changing their posture (e.g., assuming an upright posture, or lying down) and/or activity level. For example, following a triggering event, an estimate of arterial blood pressure can be determined once a minute for 10 minutes, or at 1 minute, 2 minutes, 5 minutes and 10 minutes after the triggering event. Of course, other variations are also possible, and within the scope of the present invention. It may also be that one or more specific step is performed substantially continually, but other steps are only performed in response to a triggering event or on demand.

Where at least some of the steps of FIG. 2 are triggered in response to detection of various different activity and/or posture states, information about the patient's activity and/or posture can also be stored along with estimates of the patient's arterial blood pressure, so that such information can be correlated. In other words, there could be a cross-correlation of estimates of arterial blood pressure with levels of activity and/or posture. This is also possible where the steps of FIG. 2 are not triggered in response to detection of various different activity and/or posture states, so long as activity and/or posture is also monitored.

Referring again to FIG. 2, step 214 can also include determining a rate of change of arterial blood pressure, and step 216 can include adjusting at least one pacing parameter and/or pacing configuration based on the rate of change. For instance, the magnitude of a change in arterial blood pressure may be relatively small, but the rate of change is so sudden that the patient might need compensatory pacing to elevate (or reduce) the pressure. Accordingly, in certain embodiment, modifying of a patients arterial blood pressure may be triggered if the patient's arterial blood pressure changes by at least a specified magnitude within a specified amount of time.

Embodiments of the present invention are not limited to the exact order and/or boundaries of the steps shown in FIG. 2. In fact, many of the steps can be performed in a different order than shown, and many steps can be combined, or separated into multiple steps. For another example, certain steps shown in the FIG. 2 can be separated into two or more steps. The only time order is important is where a step acts on the results of a previous step.

In accordance with specific embodiments of the present invention, estimates of arterial blood pressure, including estimates of SP, DP, PP and/or MAP (and/or changes therein) can be stored so that a physician or clinician can upload such measurements when visiting the physician or clinician. More generally, estimates of arterial blood pressure, obtained in accordance with embodiments of the present invention can be used to assess the hemodynamic status of a patient. This can include tracking a patient's cardiac disease state, including but not limited to, heart failure. For example, increases in measures of arterial blood pressure and/or circadian variability over a length of time (e.g., a month) can be interpreted as a worsening of a heart failure condition.

Figure 3:
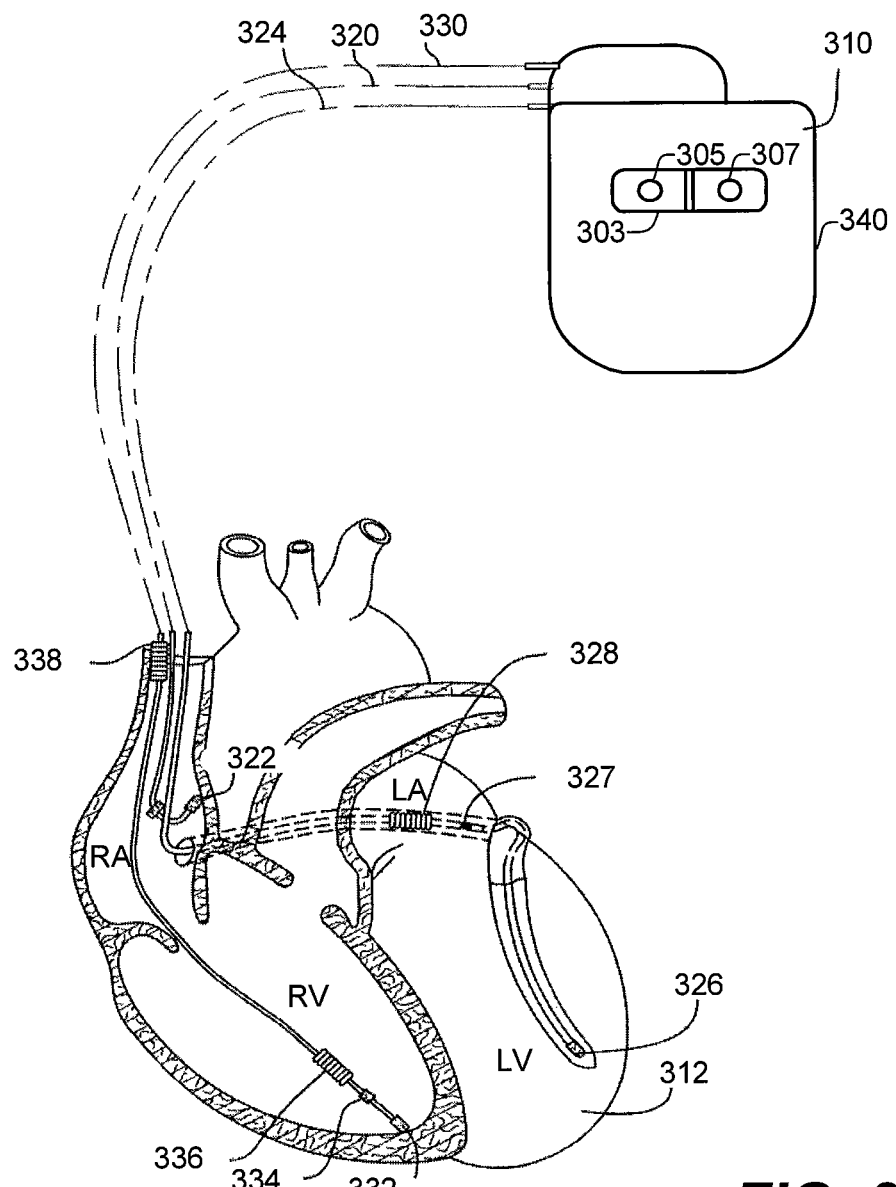
FIG. 3 illustrates an exemplary implantable cardiac stimulation device that includes a PPG sensor, and which can be used to perform various embodiments of the present invention.
Figure 4:
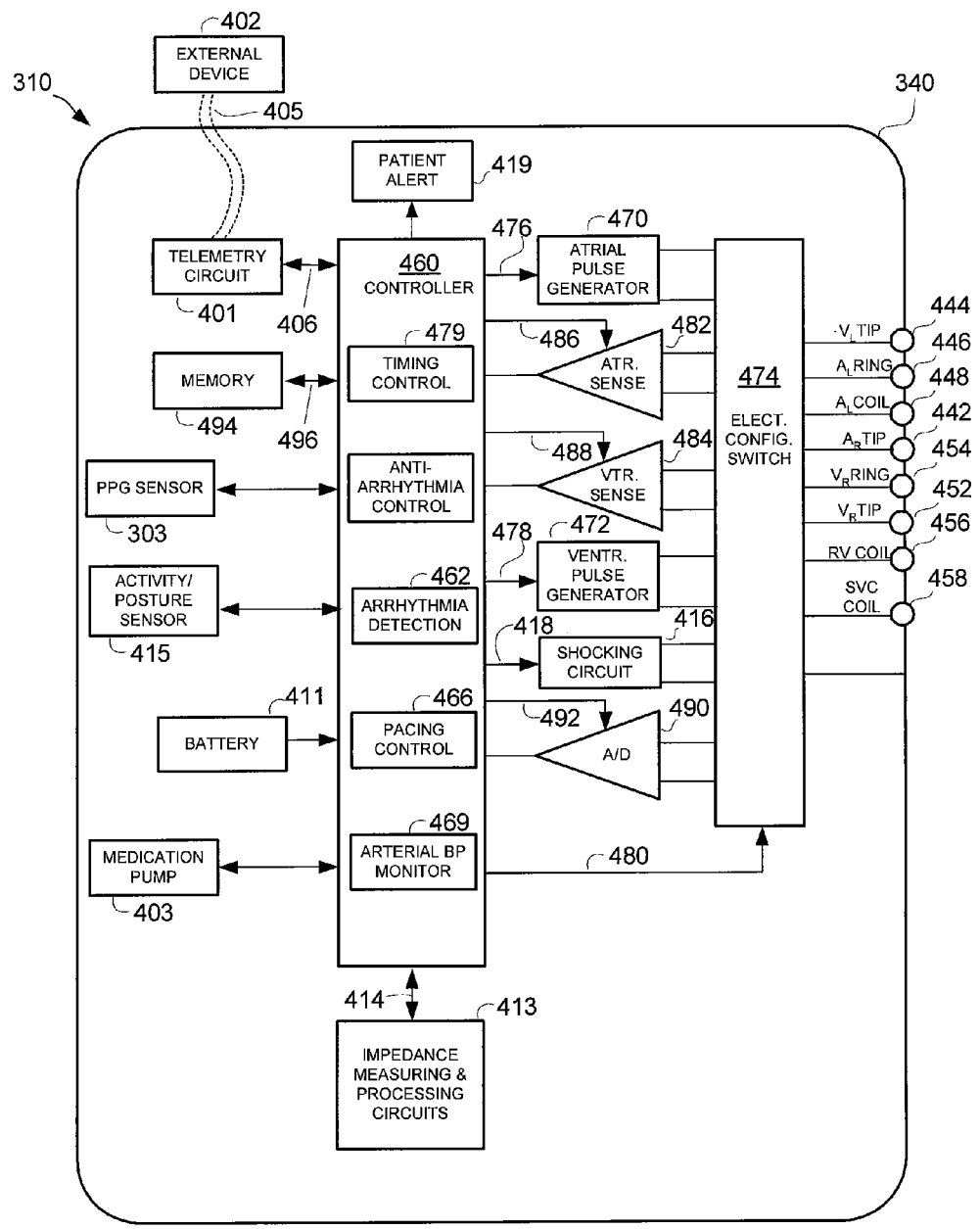
FIG. 4 is a simplified block diagram that illustrates possible components of the implantable device shown in FIG. 3.

In accordance with various embodiments, because implanted electrodes and an implanted sensor are used to estimate a patient's arterial blood pressure, the patient's arterial blood pressure can be monitored on a chronic basis. Thus, arterial blood pressure and variations (e.g., circadian variations) can be tracked to monitor a patient's evolving cardiac health, and to trigger an alert, therapy and/or adjust therapy based on the estimated arterial blood pressure. FIGS. 3 and 4 will now be used to describe an exemplary implantable system that can be used to implement embodiments of the present invention including but not limited to embodiments that monitor and modify a patient's arterial blood pressure without requiring an intravascular pressure transducer.

Exemplary Implantable System

Referring to FIG. 3, the implantable system is shown as including an implantable stimulation device 310, which can be a pacing device and/or an implantable cardioverter defibrillator (ICD). The device 310 is shown as being in electrical communication with a patient's heart 312 by way of three leads, 320, 324 and 330, which can be suitable for delivering multi-chamber stimulation and shock therapy. The leads can also be used to obtain IEGM signals, for use in embodiments of the present invention. As described below, it is also possible that one of these leads (or another lead) can include an optical sensor (also referred to as a PPG sensor) that is useful for obtaining a PPG signal, similar to signal 104 shown in FIG. 1.

In FIG. 3, the implantable device 310 is shown as having a PPG sensor 303 (also referred to as an optical sensor) attached to its housing 340. The PPG sensor 303, which can be used to obtain a PPG signal similar to signal 104 shown in FIG. 1, includes a light source 305 and a light detector 307. The light source 305 can include, e.g., at least one light-emitting diode (LED), incandescent lamp or laser diode, but is not limited thereto. The light detector 307 can include, e.g., at least one photoresistor, photodiode, phototransistor, photodarlington or avalanche photodiode, but is not limited thereto. Light detectors are often also referred to as photodetectors or photocells.

The light source 305 outputs light that is reflected or backscattered by surrounding patient tissue, and reflected/backscattered light is received by the light detector 307. In this manner, changes in reflected light intensity are detected by the light detector 307, which outputs a signal indicative of the changes in detected light. The output of the light detector 307 can be filtered and amplified. The signal can also be converted to a digital signal using an analog to digital converter, if the PPG signal is to be analyzed in the digital domain. A PPG sensor can use a single wavelength of light, or a broad spectrum of many wavelengths. Additional details of exemplary implantable PPG sensors are disclosed in U.S. Pat. Nos. 6,409,675 and 6,491,639, both entitled "Extravascular Hemodynamic Sensor" (both Turcott), which are incorporated herein by reference.

It is generally the output of the photodetector that is used to produce a PPG signal. However, there exist techniques where the output of the photodetector is maintained relatively constant by modulating the drive signal used to drive the light source, in which case the PPG signal is produced using the drive signal, as explained in U.S. Pat. No. 6,731,967, entitled "Methods and Devices for Vascular Plethysmography via Modulation of Source Intensity," (Turcott), which is incorporated herein by reference.

The extravascular PPG sensor 302 can be attached to a housing 340 of an implantable device, which as mentioned above can be, e.g., a pacemaker and/or an ICD. Exemplary details of how to attach a sensor module to an implantable cardiac stimulation device are described in U.S. Pat. No. 7,653,434, entitled "Autonomous Sensor Modules for Patient Monitoring" (Turcott et al.), which is incorporated herein by reference. It is also possible that the PPG sensor 302 be integrally part of the implantable cardiac stimulation device 310. For example, the PPG sensor 302 can be located within the housing 340 of an ICD (and/or pacemaker) that has a window through which light can be transmitted and detected. In a specific embodiment, the PPG sensor 302 has a titanium frame with a light transparent quartz or sapphire window that can be welded into a corresponding slot cut in the housing of the ICD. This will insure that the ICD enclosure with the welded PPG sensor will maintain a hermetic condition.

Where the PPG sensor is incorporated into or attached to a chronically implantable device 310, the light source 305 and the light detector 307 can be mounted adjacent to one another on the housing or header of the implantable device, or on the bottom of the device, or at any other location. The light source 305 and the light detector 307 can be placed on the side of the implantable device 310 that, following implantation, faces the chest wall, and are configured such that light cannot pass directly from the source to the detector. The placement on the side of the device 310 that faces the chest wall maximizes the signal to noise ratio by directing the signal toward the highly vascularized musculature, and shielding the source and detector from ambient light that enters the body through the skin. Alternatively, at the risk of increasing susceptibility to ambient light, the light source 305 and the light detector 307 can be placed on the face of the device 310 that faces the skin of the patient. Other variations are also possible.

In an alternative embodiment, the PPG sensor 303 (or other plethysmography sensor) is remote from the housing 340 of the device 310, but communicates with the electronics in the device housing 340 via one or more wires, optical fibers, or wirelessly (e.g., using telemetry, RF signals and/or using body fluid as a communication bus medium). This embodiment enables an obtained PPG signal to be indicative of changes in arterial blood volume at a location remote from the patient's heart, where such location is also remote from the device housing 340. If desired, multiple PPG signals can be obtained, e.g., using multiple PPG sensors at different locations.

In another embodiment, optical fibers can be used to transmit light into and detect light from tissue that is remote from the device housing, even though the light source and light detector are located within or adjacent the device housing 340. This embodiment enables an obtained PPG signal to be indicative of changes in arterial blood volume at a location remote from the patient's heart, where such location is remote from the device housing 340, even though the light source 305 and light detector 307 are not remote from the housing. The distal end of the optical fiber(s) associated with the light source can be generally parallel to the distal end of the optical fiber(s) associated with the light detector, so that the light detector detects the portion of light reflected from tissue. Alternatively, the distal end of the optical fiber(s) associated with the light source can generally face the distal end of the optical fiber(s) associated with the light detector, with tissue therebetween, so that the light detector detects the portion of light transmitted through (as opposed to reflected from) the tissue therebetween.

In an embodiment, a PPG sensor can be within or attached to a lead that may extend from a main device housing 340. Accordingly, in this embodiment, a housing of the sensor module is sized to fit within the implantable lead. For example, the PPG can be located proximal from the distal tip of the lead so that the PPG sensor is sufficiently remote from the heart that variations in pulse transmission time are detectable and meaningful. The portion of the lead that is adjacent to a window of the PPG sensor module, where light is to exit and enter, should allow the light to pass in and out of the sensor. Thus, the lead may be transparent, or include its own window, opening, or the like. The lead can including tines for attaching the lead in its desired position, but may include any other type of fixation means (e.g., a pigtail shaped fixation means), or none at all. The lead can also have a suture sleeve that enables the lead to be sutured to patient tissue. Additional details of a lead that includes an optical sensor that can be used to produce a PPG signal are provided in U.S. Pat. No. 7,660,616, entitled "Improved Multi-Wavelength Implantable Oximeter Sensor" (Poore), and U.S. Pat. No. 7,840,246, entitled "Implantable Device with a Calibration Photodetector" (Poore), which are incorporated herein by reference.

The implantable PPG sensor 303 obtains a PPG signal that after filtering is similar to signal 104 shown in FIG. 1 that pulsates over the cardiac cycle. Modulation of the signal occurs because arteries distend as the pressure wave created by the heart's pumping mechanism reaches the sensor site. Such a signal can be filtered and/or amplified as appropriate, e.g., to remove respiratory affects on the signal, and the like. Additionally, the signal can be digitized using an analog to digital converter. Exemplary techniques for performing filtering and other processing of a PPG signal (or other plethysmography signal) are explained with reference to FIGS. 5 and 6A-6E.

For much of above description, it has been assumed that the plethysmography sensor used to produce a plethysmography signal is a PPG sensor. Thus, the plethysmography signal has often been referred to as a PPG signal. However, it should be noted that other types of plethysmography sensors can alternatively be used. Thus, embodiments of the present invention should not be limited to use with PPG sensors and PPG signals. For example, electrodes of the various leads discussed below can be used to obtain an IPG signal, and the IPG signal can be used in place of the PPG signal. Details of exemplary implantable sensors that produce an impedance plethysmography signals are disclosed, e.g., in U.S. Pat. Nos. 4,674,518; 4,686,987; and 5,334,222 (all to Salo), which are incorporated herein by reference.

Still referring to FIG. 3, to sense atrial cardiac signals and to provide right atrial chamber stimulation therapy, the device 310 is coupled to an implantable right atrial lead 320 having at least an atrial tip electrode 322, which typically is implanted in the patient's right atrial appendage. To sense left atrial and ventricular cardiac signals and to provide left-chamber pacing therapy, the device 310 is coupled to a "coronary sinus" lead 324 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 324 is designed to receive atrial and ventricular cardiac signals and to deliver left ventricular pacing therapy using at least a left ventricular tip electrode 326, left atrial pacing therapy using at least a left atrial ring electrode 327, and shocking therapy using at least a left atrial coil electrode 328.

The device 310 is also shown in electrical communication with the patient's heart 312 by way of an implantable right ventricular lead 330 having, in this embodiment, a right ventricular tip electrode 332, a right ventricular ring electrode 334, a right ventricular (RV) coil electrode 336, and an SVC coil electrode 338. Typically, the right ventricular lead 330 is transvenously inserted into the heart 312 so as to place the right ventricular tip electrode 332 in the right ventricular apex so that the RV coil electrode 336 will be positioned in the right ventricle and the SVC coil electrode 338 will be positioned in the superior vena cava. Accordingly, the right ventricular lead 330 is capable of receiving cardiac signals and delivering stimulation in the form of pacing and shock therapy to the right ventricle.

FIG. 4 will now be used to provide some exemplary details of the components of the implantable devices 310. Referring now to FIG. 4, the implantable devices 310, and alternative versions thereof, can include a microcontroller 460. As is well known in the art, the microcontroller 460 typically includes a microprocessor, or equivalent control circuitry, and can further include RAM and/or ROM memory, logic and timing circuitry, state machine circuitry and/or I/O circuitry. Typically, the microcontroller 460 includes the ability to process or monitor input signals (data) as controlled by a program code stored in a designated block of memory. The details of the design of the microcontroller 460 are not critical to the present invention. Rather, any suitable microcontroller 460 can be used to carry out the functions described herein. The use of microprocessor-based control circuits for performing timing and data analysis functions are well known in the art. In specific embodiments of the present invention, the microcontroller 460 performs some or all of the steps associated with determining estimating changes in arterial blood volume and changes therein, and controlling response thereto.

Representative types of control circuitry that may be used with embodiments of the present invention include the microprocessor-based control system of U.S. Pat. No. 4,940,052 (Mann et al.) and the state-machines of U.S. Pat. No. 4,712,555 (Thornander et al.) and U.S. Pat. No. 4,944,298 (Sholder). For a more detailed description of the various timing intervals used within the pacing device and their interrelationship, see U.S. Pat. No. 4,788,980 (Mann et al.). The '052, '555, '298 and '980 patents are incorporated herein by reference.

Depending on implementation, the device 310 can be capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation.

The housing 340, shown schematically in FIG. 4, is often referred to as the "can", "case" or "case electrode" and may be programmably selected to act as the return electrode for all "unipolar" modes. The housing 340 may further be used as a return electrode alone or in combination with one or more of the coil electrodes, 328, 336 and 338, for shocking purposes. The housing 340 can further include a connector (not shown) having a plurality of terminals, 442, 444, 446, 448, 452, 454, 456, and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 322.

To achieve left atrial and ventricular sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 448, which are adapted for connection to the left ventricular tip electrode 326, the left atrial ring electrode 327, and the left atrial coil electrode 328, respectively.

To support right ventricle sensing, pacing and shocking, the connector further includes a right ventricular tip terminal ($V_R$ TIP) 452, a right ventricular ring terminal ($V_R$ RING) 454, a right ventricular shocking terminal ($R_V$ COIL) 456, and an SVC shocking terminal (SVC COIL) 458, which are adapted for connection to the right ventricular tip electrode 332, right ventricular ring electrode 334, the RV coil electrode 336, and the SVC coil electrode 338, respectively.

An atrial pulse generator 470 and a ventricular pulse generator 472 generate pacing stimulation pulses for delivery by the right atrial lead 320, the right ventricular lead 330, and/or the coronary sinus lead 324 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators, or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry 479 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, etc.) by selectively closing the appropriate combination of switches (not shown) as is known in the art.

Atrial sensing circuits 482 and ventricular sensing circuits 484 may also be selectively coupled to the right atrial lead 320, coronary sinus lead 324, and the right ventricular lead 330, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers, or shared amplifiers. The switch 474 determines the "sensing polarity" of the cardiac signal by selectively closing the appropriate switches, as is also known in the art. In this way, the clinician may program the sensing polarity independent of the stimulation polarity.

Each sensing circuit, 482 and 484, preferably employs one or more low power, precision amplifiers with programmable gain and/or automatic gain control, band-pass filtering, and a threshold detection circuit, as known in the art, to selectively sense the cardiac signal of interest. The automatic gain control enables the device 310 to deal effectively with the difficult problem of sensing the low amplitude signal characteristics of atrial or ventricular fibrillation. Such sensing circuits, 482 and 484, can be used to determine cardiac performance values used in the present invention. Alternatively, an automatic sensitivity control circuit may be used to effectively deal with signals of varying amplitude.

The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity, in the appropriate chambers of the heart. The sensing circuits, 482 and 484, in turn, receive control signals over signal lines, 486 and 488, from the microcontroller 460 for purposes of measuring cardiac performance at appropriate times, and for controlling the gain, threshold, polarization charge removal circuitry (not shown), and timing of any blocking circuitry (not shown) coupled to the inputs of the sensing circuits, 482 and 486.

For arrhythmia detection, the device 310 includes an arrhythmia detector 462 that utilizes the atrial and ventricular sensing circuits, 482 and 484, to sense cardiac signals to determine whether a rhythm is physiologic or pathologic. The timing intervals between sensed events (e.g., P-waves, R-waves, and depolarization signals associated with fibrillation) can be classified by the microcontroller 460 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy"). Additionally, the arrhythmia detector 462 can perform arrhythmia discrimination, e.g., using measures of arterial blood pressure determined in accordance with embodiments of the present invention. The arrhythmia detector 462 can be implemented within the microcontroller 460, as shown in FIG. 4. Thus, this detector 462 can be implemented by software, firmware, or combinations thereof. It is also possible that all, or portions, of the arrhythmia detector 462 can be implemented using hardware. Further, it is also possible that all, or portions, of the ischemia detector 462 can be implemented separate from the microcontroller 460.

In accordance with an embodiment of the present invention, the implantable device 310 includes an arterial blood pressure monitor 469. The arterial blood pressure monitor 469 can be used to monitor the patient's arterial blood pressure and changes therein using the techniques described above. Such techniques can include, e.g., detecting one or more predetermined feature(s) of an IEGM signal indicative of cardiac electrical activity, detecting one or more predetermined feature(s) of a plethysmography signal indicative of changes in arterial blood volume, and determining time(s) between the predetermined feature(s) of the IEGM and the predetermined feature(s) of the plethysmography signal. Such techniques also include estimating arterial blood pressure and changes therein based on such time(s). The arterial blood pressure monitor 469 can also configured to monitor changes in the patient's arterial blood pressure over a day and/or other lengths of time. Additionally, the arterial blood pressure monitor can cause the storing, within the implantable system (e.g., in memory 494), of information indicative of the monitored arterial blood pressure and changes therein so that the stored information is available for transfer to a non-implanted system. Additionally, based on the estimates of the patient's arterial blood pressure and changes therein, the monitor 469 can trigger an alert, therapy and/or adjust therapy, including but not limited to pacing therapy.

The arterial blood pressure monitor 469 can be implemented within the microcontroller 460, as shown in FIG. 4, and can be implemented by software, firmware, or combinations thereof. It is also possible that all, or portions of arterial blood pressure monitor 469 can be implemented separate from microcontroller 460.

The implantable device 310 can also include a pacing controller 466, which can adjust a pacing rate, pacing intervals and/or pacing configuration based on estimates of arterial blood pressure and/or changes therein, in accordance with embodiments of the present invention. The pacing controller 466 can be implemented within the microcontroller 460, as shown in FIG. 4. Thus, the pacing controller 466 can be implemented by software, firmware, or combinations thereof. It is also possible that all, or portions, of the pacing controller 466 can be implemented using hardware. Further, it is also possible that all, or portions, of the pacing controller 466 can be implemented separate from the microcontroller 460.

The implantable device can also include a medication pump 403, which can deliver medication to a patient if the patient's arterial blood pressure falls above, below, or outside certain thresholds or ranges. Information regarding exemplary implantable medication pumps may be found in U.S. Pat. No. 4,731,051 (Fischell) and U.S. Pat. No. 4,947,845 (Davis), both of which are incorporated by reference herein.

Still referring to FIG. 4, cardiac signals are also applied to the inputs of an analog-to-digital (ND) data acquisition system 490. The data acquisition system 490 can be configured to acquire various signal, including but not limited to, IEGM, PPG and IPG signals, convert the raw analog data into a digital signal, and store the digital signals for later processing and/or telemetric transmission to an external device 402. The data acquisition system 490 can be coupled to the right atrial lead 320, the coronary sinus lead 324, and the right ventricular lead 330 through the switch 474 to sample cardiac signals across any pair of desired electrodes.

The data acquisition system 490 can be coupled to the microcontroller 460, or other detection circuitry, for detecting an evoked response from the heart 312 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 460 detects a depolarization signal during a window following a stimulation pulse, the presence of which indicates that capture has occurred. The microcontroller 460 enables capture detection by triggering the ventricular pulse generator 472 to generate a stimulation pulse, starting a capture detection window using the timing control circuitry 479 within the microcontroller 460, and enabling the data acquisition system 490 via control signal 492 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467

(Callaghan et al.); and U.S. Pat. No. 5,350,410 (Kleks et al.), which patents are hereby incorporated herein by reference. The type of capture detection system used is not critical to the present invention.

The microcontroller 460 is further coupled to the memory 494 by a suitable data/address bus 496, wherein the programmable operating parameters used by the microcontroller 460 are stored and modified, as required, in order to customize the operation of the implantable device 310 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 312 within each respective tier of therapy. The memory 494 can also store data including information about the patient's arterial blood pressure, cardiovascular risk and/or disease progression.

The operating parameters of the implantable device 310 may be non-invasively programmed into the memory 494 through a telemetry circuit 401 in telemetric communication with an external device 402, such as a programmer, transtelephonic transceiver, or a diagnostic system analyzer. The telemetry circuit 401 can be activated by the microcontroller 460 by a control signal 406. The telemetry circuit 401 advantageously allows IEGM and status information relating to the operation of the device 310 (as contained in the microcontroller 460 or memory 494) to be sent to the external device 402 through an established communication link 404. The telemetry circuit can also be use to transmit arterial blood pressure data to the external device 402.

For examples of telemetry devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The implantable device 310 additionally includes a battery 411 which provides operating power to all of the circuits shown in FIG. 4. If the implantable device 310 also employs shocking therapy, the battery 411 should be capable of operating at low current drains for long periods of time, and then be capable of providing high-current pulses (for capacitor charging) when the patient requires a shock pulse. The battery 411 should also have a predictable discharge characteristic so that elective replacement time can be detected.

The implantable device 310 is also shown as including an activity and/or posture sensor 415. Such a sensor 415 can be a simple one dimensional sensor that converts mechanical motion into a detectable electrical signal, such as a back electro magnetic field (BEMF) current or voltage, without requiring any external excitation. Alternatively, the sensor 415 can measure multi-dimensional activity information, such as two or more of acceleration, direction, posture and/or tilt. Examples of multi-dimensional activity sensors include, but are not limited to: the three dimensional accelerometer-based position sensor disclosed in U.S. Pat. No. 6,658,292 to Kroll et al., which is incorporated herein by reference; the AC/DC multi-axis accelerometer disclosed in U.S. Pat. No. 6,466,821 to Pianca et al., which is incorporated herein by reference; and the commercially available precision dual-axis accelerometer model ADXL203 and three-axis accelerometer model ADXL346, both available from Analog Devices of Norwood, Mass. Exemplary uses of the activity/posture sensor 415 were discussed above with reference to FIG. 2.

The implantable device 310 can also include a magnet detection circuitry (not shown), coupled to the microcontroller 460. It is the purpose of the magnet detection circuitry to detect when a magnet is placed over the implantable device 310, which magnet may be used by a clinician to perform various test functions of the implantable device 310 and/or to signal the microcontroller 460 that the external programmer 402 is in place to receive or transmit data to the microcontroller 460 through the telemetry circuits 401.

As further shown in FIG. 4, the device 310 is also shown as having an impedance measuring and processing circuit 413 which is enabled by the microcontroller 460 via a control signal 414 and can be used for obtaining many types of bodily and intracardiac impedances, including a network of single- or multi-vector impedance measurements. Such impedance measurements can be used, e.g., for trending many kinds of physiological variables, and can also be used for detection of air movement in and out of the lungs, blockage of airways, lead impedance surveillance during acute and chronic phases for proper lead positioning or dislodgement; lead integrity by detecting insulation abrasion, operable electrodes, and automatically switching to an operable pair if dislodgement occurs; measuring respiration or minute ventilation; measuring thoracic impedance for determining shock thresholds; detecting when the device has been implanted; measuring cardiac stroke volume; detecting the opening of heart valves; and so forth. The impedance measuring and processing circuit 413 can also be used to produce an IPG signal. The impedance measuring circuit 413 may be coupled to the switch 474 so that any desired electrodes may be used, and networks of vectors can be selected.

In the case where the implantable device 310 is also intended to operate as an implantable cardioverter/defibrillator (ICD) device, it should detect the occurrence of an arrhythmia, and automatically apply an appropriate electrical shock therapy to the heart aimed at terminating the detected arrhythmia. To this end, the microcontroller 460 further controls a shocking circuit 416 by way of a control signal 418. The shocking circuit 416 generates shocking pulses of low (up to 0.5 Joules), moderate (0.5-10 Joules), or high energy (11 to 40 Joules), as controlled by the microcontroller 460. Such shocking pulses are applied to the patient's heart 312 through at least two shocking electrodes, and as shown in this embodiment, selected from the left atrial coil electrode 328, the RV coil electrode 336, and/or the SVC coil electrode 338. As noted above, the housing 340 may act as an active electrode in combination with the RV electrode 336, or as part of a split electrical vector using the SVC coil electrode 338 or the left atrial coil electrode 328 (i.e., using the RV electrode as a common electrode).

The above described implantable device 310 was described as an exemplary pacing device. One or ordinary skill in the art would understand that embodiments of the present invention can be used with alternative types of implantable devices. Accordingly, embodiments of the present invention should not be limited to use only with the above described device.

Processing of Plethysmography Signals

Photoplethysmography (PPG) and other plethysmography signals show changes in a patient's arterial system as a result of the patient's heart contracting, and such signals are indicative of changes in arterial blood volume. A PPG signal can be obtained using a PPG sensor, which as explained above, can be an optical sensor including a light source and a light detector. An IPG signal can be obtained using an IPG sensor, which as explained above, can include electrodes and circuitry used to measure the impedance between such electrodes. One or more such electrodes can be located on one or more leads, and/or a mechanical housing of an implanted device can act as one of the electrodes.

Figure 5:
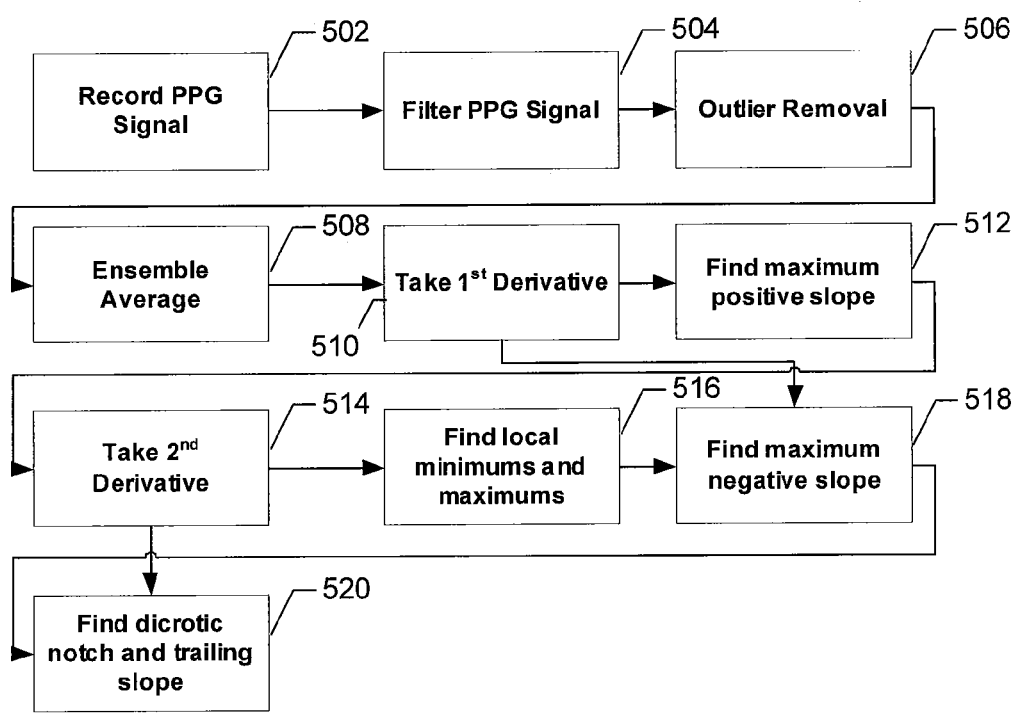
FIG. 5 is a flow diagram that is used to describe how features of a plethysmography signal can be detected in accordance with specific embodiments of the present invention.
Figure 6A:
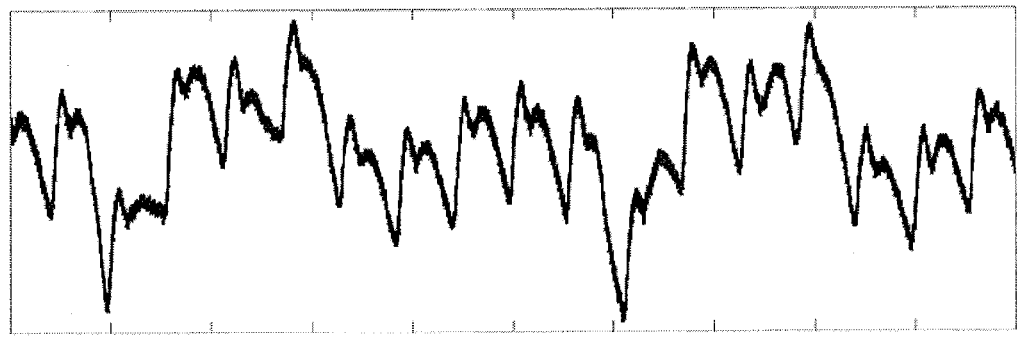
FIG. 6A illustrates an exemplary raw PPG signal over 20 seconds.

FIGS. 5 and 6A-6E will now be used to describe exemplary embodiments for obtaining a PPG signal and detecting predetermined features of the PPG signal. Similar techniques can be used to obtain an IPG signal or other plethysmography signal and detect predetermined features of the IPG signal or other plethysmography signal. Referring to FIG. 5, at step 502 a PPG signal is recorded. Recording of a PPG signal may be triggered, e.g., on an R wave, based on respiratory cycle, based on activity levels, etc. An exemplary raw PPG signal recorded over 20 second is shown in FIG. 6A.

Figure 6B:
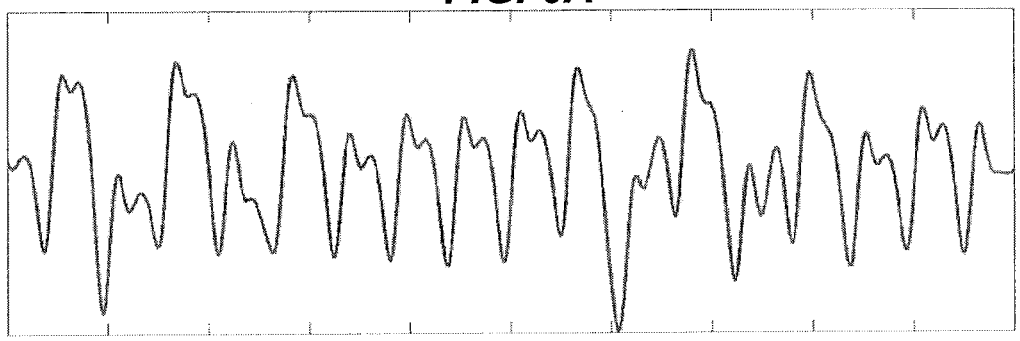
FIG. 6B illustrates the PPG signal of FIG. 6A after it has been band-passed filtered, which caused a reduction in noise due to respiration, high frequency noise, and motion artifacts.

At step 504, the PPG signal is filtered to remove respiratory noise, motion artifact, baseline drift, etc. For example, the signal can be band-pass filtered so that the pass-band is from about 0.7 to 10 Hz, although other pass bands can be used. FIG. 6B shows the raw PPG signal of FIG. 6A, after being band-passed filtered using a pass-band of about 0.7 to 10 Hz. As can be appreciated from FIG. 6B, most of the respiration signal and high frequency noise is removed by the filtering.

Figure 6C:
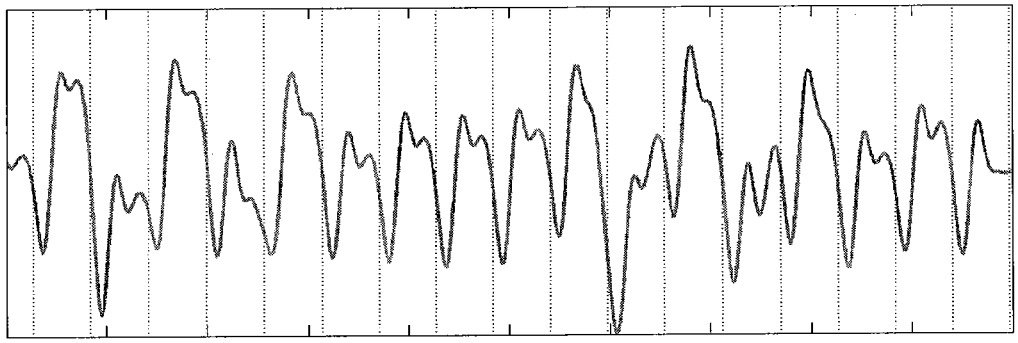
FIG. 6C is the same as FIG. 6B, but with R-wave markers added as vertical dashed lines.
Figure 6D:
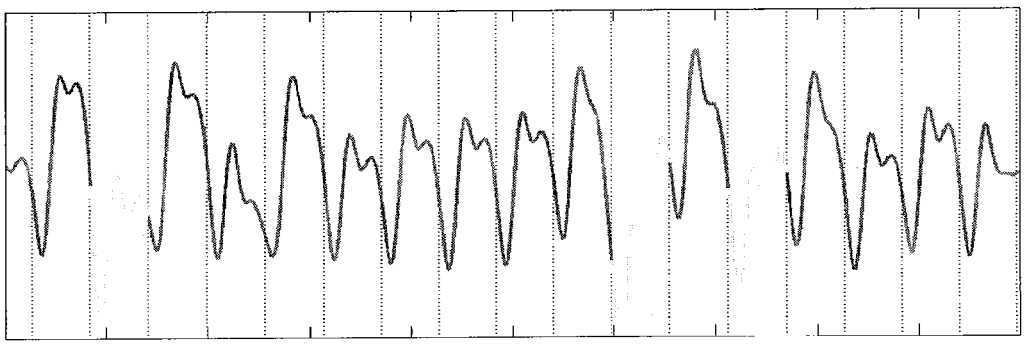
FIG. 6D is similar to FIG. 6C, but shows the removal of three outlier beats.

At step 506, an outlier removal process is performed, to remove "bad" heart beats. In an embodiment, the outlier removal can be accomplished by grouping a plurality (e.g., 20) consecutive heart beats, determining a mean of the filtered PPG signal for the plurality of heart beats, and then comparing the determined mean to individual cycles of the filtered PPG signal. Further, outlier removal can be performed by removing each cardiac cycle of the filtered PPG signal that deviates by at least a threshold amount (e.g., 3 or some other number of standard deviations) from the mean of the PPG signal for the plurality of consecutive beats. FIG. 6C show the filtered signal of FIG. 6B with R-wave markers added (shows as dashed vertical lines). FIG. 6D shows the filtered signal of FIGS. 6B and 6C with 3 "bad" beats removed as a result of an outlier removal process.

Figure 6E:
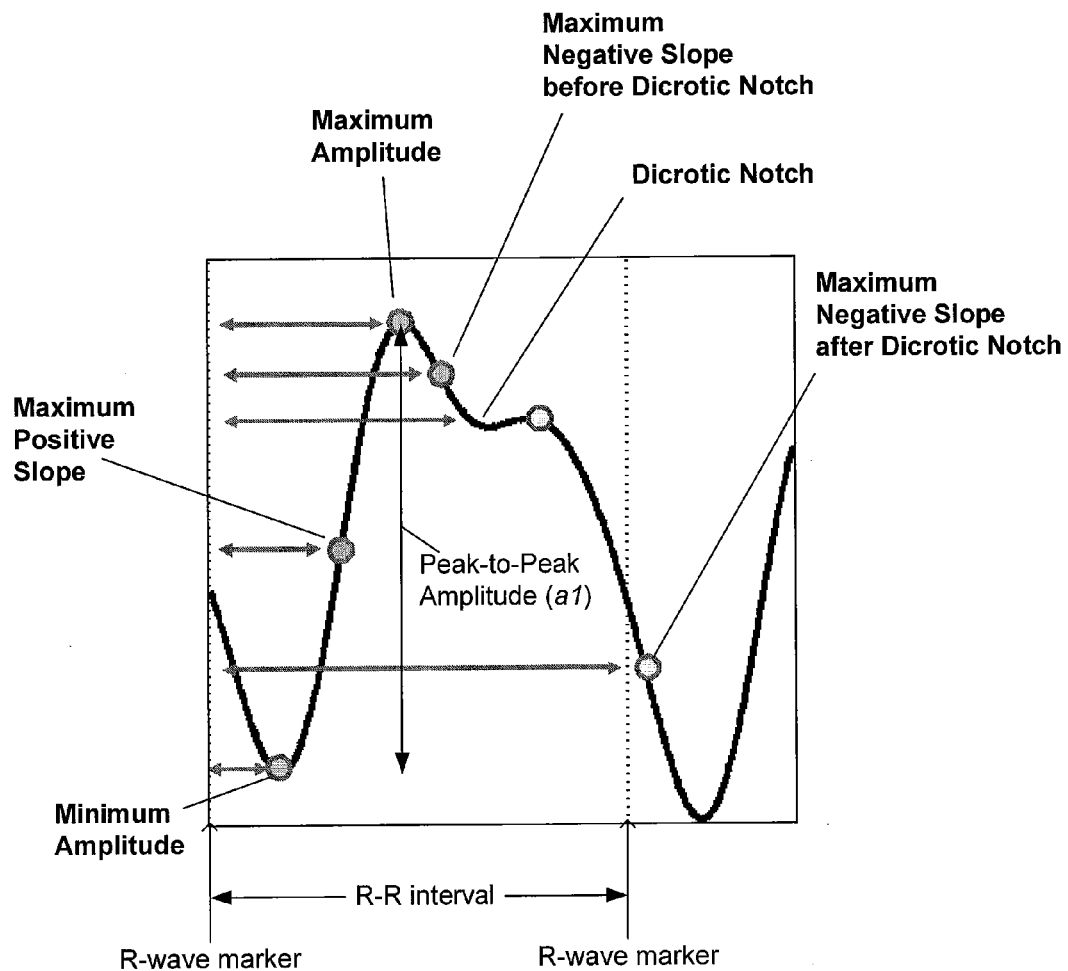
FIG. 6E illustrates an averaged PPG signal resulting from ensemble averaging the remaining cycles of FIG. 6D, and illustrates various feature of the PPG signal that can be determined and used with embodiments of the present invention.

Still referring to FIG. 5, at step 508, the cycles of the PPG signal remaining after the outlier removal step are then ensemble averaged. The result is an average representation of the PPG signal for the plurality of consecutive beats, with noise and "bad" beats removed. FIG. 6E shows an exemplary ensemble averaged PPG signal.

Thereafter, features of the PPG signal can be detected from the ensemble-averaged PPG signal. For example, as indicated at steps 510 and 512, the first derivative of the ensemble-averaged PPG signal can be determined, and the location of the maximum positive slope of the ensemble-averaged PPG signal can be detected by determining the maximum of the first derivative. Further, since it is believed that the maximum positive slope cannot be more than 70% of an R-R interval away from an R-wave, if the location of the maximum positive slope is not within 70% of an R-R interval away from an R wave, a maximum positive slope detection can be determined to be bad, and not be used.

As indicated at steps 514 and 516, the second derivative of the ensemble averaged PPG signal can be determined to find local minima and maxima. The locations of a maximum and a minimum are where the first derivative is equal to zero. The second derivative can be used to determine if a specific location is a maximum or a minimum. More specifically, if the second derivative is positive, then the point is at a minimum. If the second derivative is negative at a point, then the point is a maximum. The local minimum and local maximum that are closest to the maximum positive slope are the minimum and maximum amplitudes of the signal, which can be used, e.g., to determine the peak-to-peak amplitude of the ensemble averaged PPG signal. Further, as indicated at step 518, the maximum negative slope can be determined by identifying, from the first derivative, the local maximum that occurs after the maximum of the averaged PPG signal, but before the subsequent R-wave. As indicated at step 520, from the second derivative, the dicrotic notch can be identified by identifying the local minimum following the maximum of the averaged PPG signal, but before the subsequent R-wave. FIG. 6E shows examples of various predetermined features that can be detected. As shown in FIG. 6E a maximum downward slope can be detected prior to the dicrotic notch, as well as after the dicrotic notch.

Alternative techniques for detecting predetermined features of a PPG signal (or other plethysmography signal) can be used, such as, but not limited to, techniques that rely on template matching, wavelets, neural networks, Fast Fourier Transform (FFT) and/or time warping. Alternatively, or additionally, techniques for detecting predetermined features of a PPG signal (or other plethysmography signal) can utilize respiratory cycles and R-R intervals.

In certain embodiments, since the presence of the dicrotic notch comes and goes under different conditions, monitoring such conditions can use the presence of the dicrotic notch as a binary feature.

Embodiments of the present invention have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIG. 2. Further, it is possible to change the order of some of the steps shown in FIG. 2, without substantially changing the overall events and results. For another example, it is possible to change the boundaries of some of the blocks shown in FIG. 4.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. For use with an implantable system, a method for monitoring and modifying a patient's arterial blood pressure without requiring an intravascular pressure transducer, the method comprising:

(a) for each of a plurality of periods of time per day during which the patient's heart is being paced, (a.1) obtaining a signal indicative of electrical activity of the patient's heart, and a signal indicative of changes in arterial blood volume remote from the patient's heart;

(a.2) detecting one or more predetermined features of the signal indicative of electrical activity of the patient's heart, and one or more predetermined features of the signal indicative of changes in arterial blood volume remote from the patient's heart;

(a.3) determining one or more metrics indicative of pulse arrival time (PAT), each metric indicative of PAT determined by determining a time from one of the detected features of the signal indicative of electrical activity of the patient's heart to one of the detected features of the signal indicative of changes in arterial blood volume remote from the patient's heart; and
  (a.4) estimating the patient's arterial blood pressure based on at least one of the one or more metrics indicative of PAT;
(b) monitoring changes in the patient's arterial blood pressure based on the estimates of the patient's arterial blood pressure wherein the monitoring comprises monitoring a circadian variability of the patient's arterial blood pressure; and
(c) modifying the patient's arterial blood pressure by adjusting at least one pacing parameter and/or pacing configuration based on the monitored changes in the patient's arterial blood pressure, wherein the modifying comprises adjusting at least one pacing parameter and/or pacing configuration to increase the circadian variability if the circadian variability is below a first threshold, and adjusting at least one pacing parameter and/or pacing configuration to decrease the circadian variability if the circadian variability is above a second threshold.

2. The method of claim 1, wherein at step (c) the modifying the patient's arterial blood pressure comprises, performing one or more of the following:
  (c.1) adjusting a pacing rate;
  (c.2i) adjusting an atrio-ventricular (AV) interval; and
  (c.3) adjusting a number of pacing site within the left ventricular chamber; and
  (c.4) adjusting one or more pacing site locations within the left ventricular chamber.

3. The method of claim 1, further comprising tracking cardiovascular risk based on the monitored changes in the patient's arterial blood pressure.

4. The method of claim 1, further comprising tracking disease progression based on the monitored changes in the patient's arterial blood pressure.

5. For use with an implantable system, a method for monitoring and modifying a patient's arterial blood pressure without requiring an intravascular pressure transducer, the method comprising:
  (a) for each of a plurality of periods of time per day during which the patient's heart is being paced,
    (a.1) obtaining a signal indicative of electrical activity of the patient's heart, and a signal indicative of changes in arterial blood volume remote from the patient's heart;
    (a.2) detecting one or more predetermined features of the signal indicative of electrical activity of the patient's heart, and one or more predetermined features of the signal indicative of changes in arterial blood volume remote from the patient's heart;
    (a.3) determining one or more metrics indicative of pulse arrival time (PAT), each metric indicative of PAT determined by determining a time from one of the detected features of the signal indicative of electrical activity of the patient's heart to one of the detected features of the signal indicative of changes in arterial blood volume remote from the patient's heart; and
    (a.4) estimating the patient's arterial blood pressure based on at least one of the one or more metrics indicative of PAT;
  (b) monitoring changes in the patient's arterial blood pressure based on the estimates of the patient's arterial blood pressure; and
  (c) modifying the patient's arterial blood pressure by adjusting at least one pacing parameter and/or pacing configuration based on the monitored changes in the patient's arterial blood pressure;
  wherein:
  step (b) includes monitoring a circadian variability pattern of the patient's arterial blood pressure; and
  step (c) includes adjusting at least one pacing parameter and/or pacing configuration to cause the circadian variability pattern of the patient's arterial blood pressure to track a predetermined circadian variability pattern.

6. For use with an implantable system, a method for monitoring and modifying a patient's arterial blood pressure without requiring an intravascular pressure transducer, the method comprising:
  (a) for each of a plurality of periods of time per day during which the patient's heart is being paced,
    (a.1) obtaining a signal indicative of electrical activity of the patient's heart, and a signal indicative of changes in arterial blood volume remote from the patient's heart;
    (a.2) detecting one or more predetermined features of the signal indicative of electrical activity of the patient's heart, and one or more predetermined features of the signal indicative of changes in arterial blood volume remote from the patient's heart;
    (a.3) determining one or more metrics indicative of pulse arrival time IPAT), each metric indicative of PAT determined by determining a time from one of the detected features of the signal indicative of electrical activity of the patient's heart to one of the detected features of the signal indicative of changes in arterial blood volume remote from the patient's heart; and
    (a.4) estimating the patient's arterial blood pressure based on at least one of the one or more metrics indicative of PAT;
  (b) monitoring changes in the patient's arterial blood pressure based on the estimates of the patient's arterial blood pressure; and
  (c) modifying the patient's arterial blood pressure by adjusting at least one pacing parameter and/or pacing configuration based on the monitored changes in the patient's arterial blood pressure;
  wherein:
  step (a) also includes monitoring changes in the patient's activity level; and
  step (c) includes adjusting at least one pacing parameter and/or pacing configuration based on the monitored changes in the patient's arterial blood pressure and based on the monitored changes in the patient's activity level.

7. The method of claim 6, wherein step (c) includes at least one of the following:
  (c.1) adjusting at least one pacing parameter and/or pacing configuration to increase the patient's arterial blood pressure if an increase in the patient's arterial blood pressure is too low for the detected change in the patient's activity level; and
  (c.2) adjusting at least one pacing parameter and/or pacing configuration to decrease the patient's arterial blood pressure if the patient's arterial blood pressure is too high for the detected change in the patient's activity level.

8. For use with an implantable system, a method for monitoring and modifying a patient's arterial blood pressure without requiring an intravascular pressure transducer, the method comprising:
- (a) for each of a plurality of periods of time per day during which the patient's heart is being paced,
  - (a.1) obtaining a signal indicative of electrical activity of the patient's heart, and a signal indicative of changes in arterial blood volume remote from the patient's heart;
  - (a.2) detecting one or more predetermined features of the signal indicative of electrical activity of the patient's heart, and one or more predetermined features of the signal indicative of changes in arterial blood volume remote from the patient's heart;
  - (a.3) determining one or more metrics indicative of pulse arrival time (PAT), each metric indicative of PAT determined by determining a time from one of the detected features of the signal indicative of electrical activity of the patient's heart to one of the detected features of the signal indicative of changes in arterial blood volume remote from the patient's heart; and
  - (a.4) estimating the patient's arterial blood pressure based on at least one of the one or more metrics indicative of PAT;
- (b) monitoring changes in the patient's arterial blood pressure based on the estimates of the patient's arterial blood pressure; and
- (c) modifying the patient's arterial blood pressure by adjusting at least one pacing parameter and/or pacing configuration based on the monitored changes in the patient's arterial blood pressure;

wherein:
step (a) also includes monitoring changes in the patient's body position; and
step (c) includes adjusting at least one pacing parameter and/or pacing configuration based on the monitored changes in the patient's arterial blood pressure and based on the monitored changes in the patient's body position.

9. The method of claim 8, wherein:
step (c) includes adjusting at least one pacing parameter and/or pacing configuration to increase the patient's arterial blood pressure when a change from a supine body position to a vertical body position is detected.

10. The method of claim 8, wherein step (c) includes at least one of the following:
- (c.1) adjusting at least one pacing parameter and/or pacing configuration to increase the patient's arterial blood pressure if the change in the patient's arterial blood pressure is too low for the detected change in the patient's body position; and
- (c.2) adjusting at least one pacing parameter and/or pacing configuration to decrease the patient's arterial blood pressure if the change in the patient's arterial blood pressure is too high for the detected change in the patient's body position.

11. An implantable system configured to monitor and modify a patient's arterial blood pressure without an intravascular pressure transducer, the system comprising:
one or more pulse generator configured to pace the patient's heart;
one or more sensing circuit configured to obtaining a signal indicative of electrical activity of the patient's heart;
a plethysmography sensor configured to obtain a signal indicative of changes in arterial blood volume remote from the patient's heart;
a monitor configured to, for each of a plurality of periods of time per day during which the patient's heart is being paced,
detect one or more predetermined features of the signal indicative of electrical activity of the patient's heart;
detect one or more predetermined features of the signal indicative of changes in arterial blood volume remote from the patient's heart;
determine one or more metrics indicative of pulse arrival time (PAT) by determining a time from at least one of the detected features of the signal indicative of electrical activity of the patient's heart to at least one of the detected features of the signal indicative of changes in arterial blood volume remote from the patient's heart; and
estimate the patient's arterial blood pressure based on at least one of the one or more metrics indicative of PAT;
wherein the monitor is also configured to monitor changes in the patient's arterial blood pressure based on the estimates of the patient's arterial blood pressure; and
a controller configured to modify the patient's arterial blood pressure by adjusting at least one pacing parameter and/or pacing configuration based on the monitored changes in the patient's arterial blood pressure.

12. The implantable system of claim 11, wherein:
the controller is configured to modify arterial blood pressure by adjusting a pacing rate, adjusting an atrio-ventricular (AV) interval, adjusting a number of pacing sites within the left ventricular chamber, and adjusting one or more pacing site locations within the left ventricular chamber.

13. The implantable system of claim 11, wherein:
the monitor is configured to monitor a circadian variability of the patient's arterial blood pressure; and
the controller is configured to
adjust at least one pacing parameter and/or pacing configuration to increase the circadian variability if the circadian variability is below a first threshold; and
adjust at least one pacing parameter and/or pacing configuration to decrease the circadian variability if the circadian variability is above a second threshold.

14. The implantable system of claim 11, wherein:
the monitor is configured to monitor a circadian variability pattern of the patient's arterial blood pressure; and
the controller is configured to adjust at least one pacing parameter and/or pacing configuration to cause the circadian variability pattern of the patient's arterial blood pressure to track a predetermined circadian variability pattern.

15. The implantable system of claim 11, further comprising:
an activity sensor configured to detect changes in the patient's activity level;
wherein the monitor is configured to
adjust at least one pacing parameter and/or pacing configuration to increase the patient's arterial blood pressure if an increase in the patient's arterial blood pressure is too low for the detected change in the patient's activity level; and
adjust at least one pacing parameter and/or pacing configuration to decrease the patient's arterial blood pressure if the patient's arterial blood pressure is too high for the detected change in the patient's activity level.

16. The implantable system of claim 11, further comprising:
- a posture sensor configured to monitor changes in the patient's body position;
- wherein the controller is configured to
- adjust at least one pacing parameter and/or pacing configuration to increase the patient's arterial blood pressure if the change in the patient's arterial blood pressure is too low for the detected change in the patient's body position; and
- adjust at least one pacing parameter and/or pacing configuration to decrease the patient's arterial blood pressure if the change in the patient's arterial blood pressure is too high for the detected change in the patient's body position.

17. The implantable system of claim 11, wherein the monitor is also configured to track cardiovascular risk and/or disease progression based on the monitored changes in the patient's arterial blood pressure.

18. An implantable system configured to monitor and modify a patient's arterial blood pressure without an intravascular pressure transducer, the system comprising:
- one or more sensing circuit configured to obtaining a signal indicative of electrical activity of the patient's heart;
- a plethysmography sensor configured to obtain a signal indicative of changes in arterial blood volume remote from the patient's heart;
- a monitor configured to, for each of a plurality of periods of time,
- determine one or more metrics indicative of pulse arrival time (PAT), each of which are indicative of how long it takes a pulse wave to travel from the patient's aorta to a location remote from the patient's aorta; and
- estimate the patient's arterial blood pressure based on at least one of the one or more metrics indicative of PAT;
- a controller configured to modify the patient's arterial blood pressure by initiating and/or adjusting pacing and/or other therapy based on the estimates of the patient's arterial blood pressure and/or changes therein.

* * * * *